US012337162B2

(12) United States Patent
Hendrix et al.

(10) Patent No.: US 12,337,162 B2
(45) Date of Patent: Jun. 24, 2025

(54) MEDICAL WEIGHING SYSTEMS

(71) Applicant: Medline Industries, LP, Northfield, IL (US)

(72) Inventors: Heidi Frances Hendrix, Brookhaven, GA (US); David Richard Rawlings, Cumming, GA (US); Sean Corrigan, Chicago, IL (US); David B. Richmond, Fairfax, VA (US); David Davis, Herndon, VA (US)

(73) Assignee: Medline Industries, LP, Northfield, IL (US)

( * ) Notice: Subject to any disclaimer, the term of this patent is extended or adjusted under 35 U.S.C. 154(b) by 931 days.

(21) Appl. No.: 17/214,647

(22) Filed: Mar. 26, 2021

(65) Prior Publication Data

US 2021/0213212 A1 Jul. 15, 2021

Related U.S. Application Data

(63) Continuation of application No. 15/469,487, filed on Mar. 24, 2017, now Pat. No. 11,013,867.

(Continued)

(51) Int. Cl.
*A61M 5/44* (2006.01)
*A61B 46/10* (2016.01)
(Continued)

(52) U.S. Cl.
CPC .............. *A61M 5/445* (2013.01); *A61B 46/10* (2016.02); *A61B 50/13* (2016.02); *A61M 3/0208* (2014.02);
(Continued)

(58) Field of Classification Search
CPC . A61B 46/10; A61B 50/13; A61F 7/00; A61F 7/0085; A61F 7/086; A61M 19/00;
(Continued)

(56) References Cited

U.S. PATENT DOCUMENTS 3,777,749 A 12/1973 Collins
4,476,946 A * 10/1984 Smith ................... G01G 19/52
177/144

(Continued)

FOREIGN PATENT DOCUMENTS

AU 2013340326 A1 3/2015
AU 2016200812 B2 11/2016
(Continued)

OTHER PUBLICATIONS

European Patent Application No. 17771304.7, Extended European Search Report mailed Sep. 3, 2019, 6 pages.
(Continued)

*Primary Examiner* — Sang Y Paik
(74) *Attorney, Agent, or Firm* — SandBright, PLLC; Robert Dan Spendlove

(57) ABSTRACT

A weighing system for medical applications may include a basin that has a base and a sloped sidewall that collectively form a bounded cavity with open top surface that receives and holds the material to be weighed. The basin may be free floating above the weighing device within a restricted range of travel. In some examples, the weighing system includes a thermal treatment device to adjust the temperature of the material in the basin. The rate at which heat is delivered to the basin may vary depending on the weight of the contents in the basin.

18 Claims, 13 Drawing Sheets

Related U.S. Application Data

(60) Provisional application No. 62/313,249, filed on Mar. 25, 2016.

(51) Int. Cl.

| | | |
|---|---|---|
| *A61B 50/13* | (2016.01) | |
| *A61M 3/02* | (2006.01) | |
| *A61M 19/00* | (2006.01) | |
| *F24H 1/00* | (2022.01) | |
| *G01G 17/04* | (2006.01) | |
| *G01G 19/52* | (2006.01) | |
| *G01G 21/22* | (2006.01) | |

(52) U.S. Cl.
CPC .......... *A61M 3/0212* (2014.02); *A61M 3/022* (2014.02); *A61M 3/0266* (2013.01); *A61M 19/00* (2013.01); *F24H 1/0072* (2013.01); *G01G 17/04* (2013.01); *G01G 19/52* (2013.01); *G01G 21/22* (2013.01); *A61M 2205/3306* (2013.01); *A61M 2205/3334* (2013.01); *A61M 2205/3368* (2013.01); *A61M 2205/3389* (2013.01); *A61M 2205/3393* (2013.01); *A61M 2205/3569* (2013.01); *A61M 2205/3576* (2013.01); *A61M 2205/3606* (2013.01); *A61M 2205/3653* (2013.01); *A61M 2205/50* (2013.01); *A61M 2205/502* (2013.01); *A61M 2205/52* (2013.01); *A61M 2205/60* (2013.01); *A61M 2205/8206* (2013.01); *A61M 2205/8262* (2013.01)

(58) Field of Classification Search
CPC .. A61M 2205/3306; A61M 2205/3334; A61M 2205/3368; A61M 2205/3389; A61M 2205/3393; A61M 2205/3569; A61M 2205/3576; A61M 2205/3606; A61M 2205/3653; A61M 2205/50; A61M 2205/502; A61M 2205/52; A61M 2205/60; A61M 2205/8206; A61M 2205/8262; A61M 3/0208; A61M 3/0212; A61M 3/022; A61M 3/0266; A61M 5/445; F24H 1/0072; G01F 13/00; G01F 22/00; G01F 23/20; G01F 23/30; G01G 17/04; G01G 19/52; G01G 21/22
USPC .............. 392/444.1, 458; 219/385, 406, 407, 219/492–494, 518

See application file for complete search history.

(56) References Cited

U.S. PATENT DOCUMENTS

| | | | |
|---|---|---|---|
| 4,628,186 A | 12/1986 | Bergemann et al. | |
| 4,934,152 A | 6/1990 | Templeton | |
| 4,967,061 A * | 10/1990 | Weber, Jr. .......... | G05D 23/1928 219/521 |
| 5,163,299 A | 11/1992 | Faries, Jr. et al. | |
| 5,331,820 A | 7/1994 | Faries, Jr. et al. | |
| 5,333,326 A | 8/1994 | Faries, Jr. et al. | |
| 5,400,616 A | 3/1995 | Faries, Jr. et al. | |
| 5,402,644 A | 4/1995 | Faries, Jr. et al. | |
| 5,429,801 A | 7/1995 | Faries, Jr. et al. | |
| 5,435,322 A | 7/1995 | Marshall | |
| 5,443,082 A | 8/1995 | Mewburn | |
| 5,457,962 A | 10/1995 | Faries, Jr. et al. | |
| 5,502,980 A | 4/1996 | Faries, Jr. et al. | |
| 5,522,095 A | 6/1996 | Faries, Jr. et al. | |
| 5,524,643 A | 6/1996 | Faries, Jr. et al. | |
| 5,551,240 A | 9/1996 | Faries, Jr. et al. | |
| 5,615,423 A | 4/1997 | Faries, Jr. et al. | |
| 5,653,938 A | 8/1997 | Faries, Jr. et al. | |
| 5,809,788 A | 9/1998 | Faries, Jr. et al. | |
| 5,816,252 A | 10/1998 | Faries, Jr. et al. | |
| 5,857,467 A | 1/1999 | Faries, Jr. et al. | |
| 5,879,621 A | 3/1999 | Faries, Jr. et al. | |
| 5,893,396 A | 4/1999 | Vagle | |
| 5,950,438 A | 9/1999 | Faries, Jr. et al. | |
| 6,003,328 A | 12/1999 | Faries, Jr. et al. | |
| 6,035,855 A | 3/2000 | Faries, Jr. et al. | |
| 6,087,636 A | 7/2000 | Faries, Jr. et al. | |
| 6,091,058 A | 7/2000 | Faries, Jr. et al. | |
| 6,255,627 B1 | 7/2001 | Faries et al. | |
| 6,371,121 B1 | 4/2002 | Faries et al. | |
| 6,615,836 B1 | 9/2003 | Griesbach et al. | |
| 6,649,040 B1 | 11/2003 | Mirchi et al. | |
| 6,810,881 B2 | 11/2004 | Faries et al. | |
| 6,860,271 B2 | 3/2005 | Faries, Jr. et al. | |
| 6,910,485 B2 | 6/2005 | Faries, Jr. et al. | |
| 6,918,395 B2 | 7/2005 | Faries, Jr. et al. | |
| 7,128,275 B2 | 10/2006 | Kammer et al. | |
| 7,176,030 B2 | 2/2007 | Faries, Jr. et al. | |
| D546,943 S | 7/2007 | Kammer et al. | |
| D546,944 S | 7/2007 | Kammer et al. | |
| D547,444 S | 7/2007 | Kammer et al. | |
| 7,347,210 B2 | 3/2008 | Faries, Jr. et al. | |
| 7,350,373 B1 | 4/2008 | Faries, Jr. et al. | |
| D568,989 S | 5/2008 | Kammer et al. | |
| D569,970 S | 5/2008 | Kammer et al. | |
| 7,398,738 B2 | 7/2008 | Newhouse et al. | |
| 7,418,966 B2 | 9/2008 | Faries, Jr. et al. | |
| 7,441,714 B2 | 10/2008 | Kammer et al. | |
| 7,459,657 B2 | 12/2008 | Kammer et al. | |
| 7,560,667 B2 | 7/2009 | Kammer et al. | |
| 7,600,423 B1 | 10/2009 | Fluhler et al. | |
| 7,671,302 B1 | 3/2010 | Faries, Jr. et al. | |
| 7,728,262 B1 | 6/2010 | Faries, Jr. et al. | |
| 7,854,387 B2 | 12/2010 | Kammer et al. | |
| 7,903,957 B2 | 3/2011 | Kammer et al. | |
| 7,959,860 B2 | 6/2011 | Faries, Jr. et al. | |
| 8,138,454 B2 | 3/2012 | Kammer et al. | |
| 8,148,667 B2 | 4/2012 | Faries, Jr. et al. | |
| 9,367,061 B2 | 6/2016 | Miller et al. | |
| 2003/0089531 A1 | 5/2003 | Montagnino et al. | |
| 2004/0208780 A1 | 10/2004 | Faries, Jr. et al. | |
| 2004/0247016 A1 | 12/2004 | Faries, Jr. et al. | |
| 2006/0291533 A1 | 12/2006 | Faries et al. | |
| 2008/0152937 A1 | 6/2008 | Kammer et al. | |
| 2008/0213874 A1 | 9/2008 | Mitchell et al. | |
| 2009/0112057 A1 | 4/2009 | Kammer et al. | |
| 2009/0113618 A1 | 5/2009 | Slayton | |
| 2009/0255540 A1 | 10/2009 | Faries, Jr. | |
| 2010/0211355 A1 | 8/2010 | Horst et al. | |
| 2010/0228222 A1 | 9/2010 | Williams et al. | |
| 2013/0048625 A1* | 2/2013 | Sladecek .............. | A47J 36/321 374/E7.042 |
| 2013/0152946 A1 | 6/2013 | Sosnowski | |
| 2013/0197437 A1 | 8/2013 | Faries et al. | |
| 2014/0067025 A1 | 3/2014 | Levinson et al. | |
| 2014/0208986 A1 | 7/2014 | DesRoches et al. | |
| 2014/0246119 A1 | 9/2014 | Lee | |
| 2015/0054625 A1 | 2/2015 | Blair et al. | |
| 2015/0168207 A1 | 6/2015 | Pollock et al. | |
| 2018/0360023 A1 | 12/2018 | McPherson et al. | |
| 2019/0090972 A1 | 3/2019 | Hendrix et al. | |

FOREIGN PATENT DOCUMENTS

| | | |
|---|---|---|
| CA | 2620906 A1 | 3/2006 |
| CA | 2620907 A1 | 3/2006 |
| CN | 201384756 Y | 1/2010 |
| CN | 101669122 A | 3/2010 |
| CN | 202885227 U | 4/2013 |
| CN | 104703471 A | 6/2015 |
| CN | 104800911 A | 7/2015 |
| CN | 105091050 A | 11/2015 |
| EP | 401591 A2 | 12/1990 |
| EP | 1647217 A1 | 4/2006 |
| EP | 1731068 A1 | 12/2006 |
| IN | 103442745 A | 12/2013 |
| JP | S61-149828 A | 7/1986 |
| JP | 2002048344 A | 2/2002 |

(56) References Cited

FOREIGN PATENT DOCUMENTS

| | | |
|---|---|---|
| JP | 2004333048 A | 11/2004 |
| JP | 2011045756 A | 3/2011 |
| JP | 2012055411 A | 3/2012 |
| JP | 2013167522 A | 8/2013 |
| RU | 2219950 C2 | 12/2003 |
| RU | 2275826 C2 | 5/2006 |
| WO | 2005056089 A2 | 6/2005 |
| WO | 2009152568 A1 | 12/2009 |
| WO | 2011000919 A1 | 1/2011 |
| WO | 2014134674 A1 | 9/2014 |

OTHER PUBLICATIONS

International Patent Application No. PCT/US2017/024183, International Search Report and Written Opinion mailed Jul. 17, 2017, 11 pages.
International Patent Application No. PCT/US2017/024185, International Search Report and Written Opinion mailed Jul. 17, 2017, 12 pages.
European Patent Application No. 20195034.2, Extended European Search Report mailed Jan. 11, 2021, 9 pages.

* cited by examiner

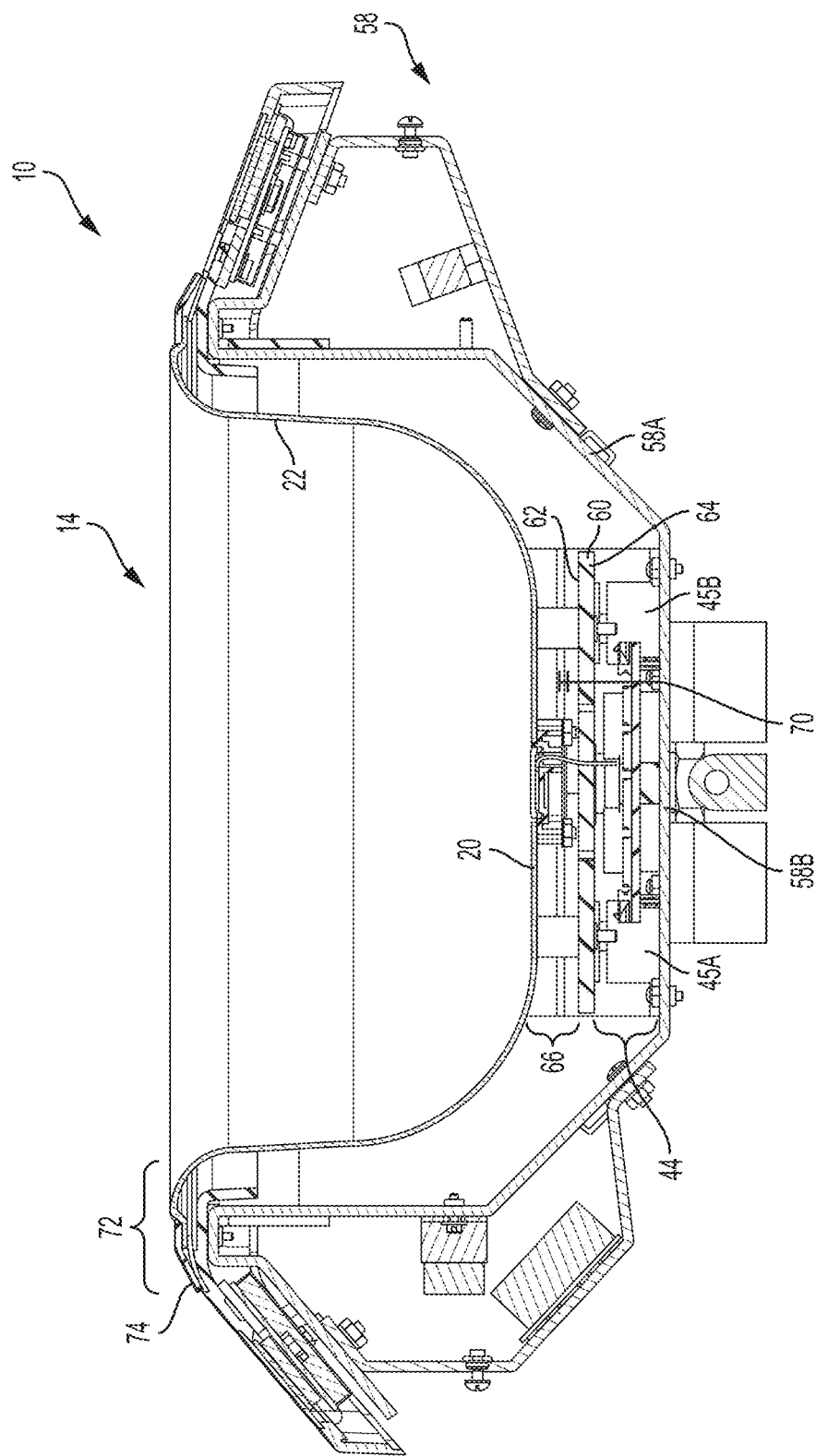

MEDICAL WEIGHING SYSTEMS

CROSS-REFERENCE

This application is a continuation of U.S. patent application Ser. No. 15/469,487, filed Mar. 24, 2017, which claims priority to U.S. Provisional Patent Application No. 62/313,249, filed Mar. 25, 2016. The entire contents of each of these applications are incorporated herein by reference.

TECHNICAL FIELD

This disclosure relates to weighing systems for medical applications, including weighing systems that incorporate temperature adjustment functionality.

BACKGROUND

Surgical fluid is used during a variety of different medical procedures. For example, saline is often used during surgery to irrigate the site of operation. The saline can be poured on the site of surgery to flush the region of blood and other bodily matter, providing the clinician with a clear view of the region being operated upon and clean surfaces for performing the operation. As another example, surgical fluid may be frozen into a slush that is introduced into a particular region of the body. The slush can provide localized hypothermia therapy, cooling the region of the body or organ around which the slush is placed. This can be useful to temporarily reduce the amount of oxygenated blood needed by the body, such as in emergencies like cardiac arrest or severe head trauma.

Controlling the temperature of surgical fluid prior to introduction into the body can be useful to help ensure a safe and efficacious medical procedure. For example, in the case of surgical slush, the surgical fluid may be cooled to a temperature sufficient to provide a slush but not so low that the surgical slush reaches organ-damaging temperatures. As another example, in the case of liquid irrigation, the surgical fluid may be heated above room temperature before being introduced into the patient's body.

Anesthetized patients cannot regulate their body temperature. This is because the portion of the brain that regulates body temperature shuts down with anesthesia. If surgical irrigation fluid is not heated before being introduced into the patient, the surgical fluid can cool the patient's core body temperature. For procedures that take a longer amount of time or involve larger amounts of irrigation fluid, the cumulative cooling effect can increase the risk of unintended hypothermia. For this reason, the surgical fluid may be heated to a temperature around the patient's standard body temperature (98.6 degrees Fahrenheit) before introducing the fluid into the patient. This can help minimize the risks of unintended hypothermia.

Independent of whether surgical fluid is heated or cooled before being introduced into a patient, a nurse or other clinician in charge of surgical fluid during the procedure may monitor the amount of fluid introduced into the patient. Typically, surgical fluid comes prepackaged in bottles of standard size, and the clinician may monitor the number of bottles used during a procedure to determine the amount of fluid introduced into the patient. The clinician may monitor the amount of fluid used to ensure that too much fluid is not introduced into the patient and/or that a proportional amount of fluid is withdrawn from the patient using a suction device.

SUMMARY

In general, this disclosure is directed to devices, systems, and techniques for monitoring and/or determining the amount of a material in a surgical environment and, optionally, adjusting the temperature of such material. In some configurations, the device is designed to receive a surgical fluid to be used during a medical procedure, heat the fluid to a temperature suitable to be introduced into a mammalian patient, and actively track the volume of fluid removed from the device during the procedure. The device may track the volume of fluid introduced and/or removed from the device using any suitable volume measurement device. For example, the volume measurement device may be implemented by measuring the weight of the fluid and then determining volume based on a programmed density of the fluid, by measuring the height of the fluid in the basin, by measuring the volume of fluid dispensed through a filling inlet and/or a dispensing outlet, or by yet other volume measurement arrangements. When configured to measure weight, the device may provide a convenient weighing apparatus for weighing objects in the surgical environment, such as specimens extracted from a patient. For these weighing applications, the device may or may not include temperature adjustment functionality.

In some examples, a system is configured as a surgical fluid warmer that includes a basin that receives and holds surgical fluid. The basin is supported on a base, such as a movable base mounted on caster wheels to allow the system to easily move from one location to another. The system includes a heater thermally coupled to the basin and configured to heat surgical liquid placed in the basin to a target temperature. In addition, the system includes a volume measurement device. The volume measurement device is positioned to obtain volume information concerning the volume of surgical fluid added to the basin. For example, in different applications, the volume measurement device may be implemented using a load cell that indirectly measures volume by measuring weight of the basin and contents therein, a float that rises and falls based on the level of surgical fluid in the basin, or other sensor that measures the volume of surgical fluid in the basin. In either configuration, the system can also include a display that displays the volume of surgical fluid used during a procedure. The display may update in substantially real-time as fluid is removed from the basin and introduced into the patient, giving the clinician timely and accurate information for making clinical decisions.

In practice, monitoring the total volume surgical fluid withdrawn from a surgical fluid warmer basin can be challenging because the basin may be refilled during a procedure and/or non-fluid components may be periodically added and withdrawn from the basin during the procedure. For example, a clinician may place a sterile asepto bulb syringe and/or a sterile graduated measuring container into the basin and then use these tools during the procedure to transfer fluid from the basin to the patient. The apparent volume of surgical fluid in the basin will rise or fall depending on whether the tools are in the basin or out of the basin.

In some systems according to the disclosure, a user interface is provided that a clinician can interact with to inform the system whether new fluid is being added to the basin, whether a tool is being added or removed from the basin, or the like. For example, the user interface may include a user-manipulable input, such as a button on a console or touchscreen display, or other mechanism (e.g., foot pedal), that a user can press to inform the system that a tool is to be added or removed from the basin. The user interface may include a separate user-manipulable input that the user can press to inform the system that additional surgical fluid is to be added to the basin. Additionally or alternatively, the system may include a user interface that receives audible input or commands from the user and/or an optical detector that detects user behavior or commands to determine when surgical fluid or a tool are added or removed from the basin.

In operation, a controller associated with the system can monitor the volume of fluid in the basin based on feedback from the volume measurement device. The controller can track reductions in the volume of fluid and attribute those reductions to fluid being removed and introduced into the patient. When the controller is informed via the user interface that fresh fluid is to be added to the basin, the controller can identify that corresponding changes in the measured volume of fluid in the basin are associated with new fluid being added to the basin and not fluid previously withdrawn from the basin being returned from the basin. Even if the controller is not informed via the user interface that fresh fluid is to be added to the basin, if the controller detects an increased volume of fluid in the basin (e.g., above a magnitude typically associated with a tool or fluid being returned to the basin), the controller may designate the increased volume as being fresh fluid added. In applications where the system is also configured to check tools in and out of the basin, the controller may be informed via the user interface that a tool is to be added or removed from the basin. When so informed, the controller can disregard corresponding changes in the measured volume of fluid in the basin as being associated with the addition or removal of the tool from the basin rather than surgical fluid.

In applications where the system monitors the volume of fluid removed from the basin by detecting changes in weight, the system may be designed with a floating basin configuration that allows the basin to move relative to one or more load cells. The basin may be allowed to move upwardly and downwardly with respect to ground over a restricted range of travel as the weight of contents placed in the basin vary. In some configurations, the basin is mounted to a mounting plate that presses against the one or more load cells with an air gap formed between the basin and the load cell(s). This air gap, which may be entirely devoid of material or may be filled with a material of less thermal conductivity than the basin itself, can help thermally isolate the basin from the load cell(s). In operation, the basin and contents therein may be heated while the weight of the basin and contents are measured by the load cell(s). Creating an air gap between the basin and load cell(s) can help minimize the extent to which the load cells are heated as the basin and contents are heated. In turn, this may help reduce or eliminate weighing inaccuracies caused by the load cell(s) increasing in temperature.

Independent of the specific configuration of the basin relative to the load cell(s), in applications where the system is configured to measure the amount of material in the basin and also heat the material, the system may use quantity and temperature measurements to control the heating. For example, the system may receive information from the system concerning the amount of material in the basin and also concerning a measured temperature of the material in the basin. If the system determines that the amount of material in the basin is comparatively small (e.g., below a threshold) the system may control the heater to provide a different rate of heating than if the system determines the amount of material in the basin is larger. The system can control the heater to heat the material in the basin until the material reaches a measured target temperature. In some examples, the system modulates and reduces the rate at which the heater delivers heat as the material in the basin approaches (e.g., gets within a threshold range) of the target temperature. Controlling the rate of heating based on the amount of material in the basin and/or measured temperature of the material can be useful to prevent overheating of the material, such as during startup when the material is heating from ambient temperature.

A thermal treatment system according to the disclosure can have a variety of other features in addition to or in lieu of volume measurement and tracking capabilities. For example, the system may include a basin that is configured to receive a disposable drape. The drape may conform to the shape of the basin and have a skirt that hangs down the side of the basin. Installation of the drape in the basin can establish a sterile field for subsequent introduction of the sterile surgical fluid and/or tools in the basin and drape contained therein.

To help ensure that the drape placed in the basin is suitable and compatible with the system—for example, can tolerate the thermal conditions generated by the system without degrading—the temperature management system may include a non-contact reader. The non-contact reader can be implemented as part of a system intended to function with corresponding disposable drapes containing non-contact tags. In operation, when a clinician places a drape in the basin, the non-contact reader can emit a signal searching for a corresponding tag on the drape. If the system reads identification information off of the non-contact tag on the drape and confirms that the drape is authorized for use, the system can proceed with operation. On the other hand, if the system determines that the drape lacks a non-contact tag or that the identification information on the tag is not authorized, the system may prohibit further operation. In one example, the non-contact reader and corresponding tag can be implemented using near field communication (NFC) technology. A system according to the disclosure can have additional or different features, as described herein.

In one example, a system for thermally treating surgical fluid is described that includes a basin, a thermal treatment device, a volume measurement device, and a controller. The basin is configured to receive and hold a surgical fluid. The thermal treatment device is thermally coupled to the basin and configured to adjust a temperature of the surgical fluid in the basin. The volume measurement device is positioned to obtain volume information concerning a volume of surgical fluid in the basin. According to the example, the controller is configured to receive volume measurement information from the volume measurement device concerning the volume of surgical fluid in the basin during the course of a procedure. The controller is further configured to determine the volume of surgical fluid removed from the basin during the procedure.

In another example, a method is described that includes engaging a user interface on a device for thermally treating surgical fluid, thereby informing the device that surgical fluid is to be added to the device. The method further includes adding the surgical fluid to a basin of the device and engaging the user interface of the device, thereby informing the device that the surgical fluid has been added to the device. The method involves removing surgical fluid from the basin and displaying by the device a volume of surgical fluid removed from the basin.

In another example, a system for heating surgical fluid is described. The system includes a base mounted on wheels and a basin supported by and vertically elevated above the base, with the basin being configured to receive and hold a surgical fluid. The system also includes a heater thermally coupled to the basin and configured to increase a temperature of the surgical fluid in the basin, and a weighing device positioned to obtain weight information concerning a weight of the basin and any contents thereof. The system further includes a user interface configured to receive a user indication that surgical fluid is to be added to the basin. The controller is configured to receive weight measurement information from the weight measurement device concerning the weight of surgical fluid in the basin during the course of a procedure, receive at least one indication via the user interface that the medical tool is to be added or removed from the basin during the procedure, and determine the volume of surgical fluid used during the procedure based on the received weight measurement information and the received at least one indication.

In another example, a thermal treatment system is described that includes a fluid reservoir, a thermal treatment device, a mounting plate, and a weight measurement device. The fluid reservoir has a base and at least one sidewall that are configured to receive and hold a material. The thermal treatment device is thermally coupled to the fluid reservoir and configured to adjust a temperature of the material in the fluid reservoir. The mounting plate has a first side and a second side opposite the first side. The mounting plate is attached to the fluid reservoir with an air gap formed between the first side of the mounting plate and the base of the fluid reservoir. The weight measurement device is positioned on the second side of the mounting plate that is configured to measure a weight of the fluid reservoir and any contents therein.

In a further example, a thermal treatment system is described. The thermal treatment system includes a basin configured to receive and hold a material to be heated, a thermal treatment device thermally coupled to the basin and configured to adjust a temperature of the material to be heated in the basin, a weight measurement device positioned to measure a weight of the basin and any contents therein, a user interface, and a controller. The controller is in communication with the user interface, the thermal treatment device, and the weight measurement device. The example specifies that the controller is configured to receive a target temperature via the user interface to which any contents in the basin are to be heated, receive weight measurement information from the weight measurement device concerning the weight of the basin and any contents therein, and receive temperature measurement information from the temperature sensor concerning a measured temperature of any contents in the basin. The controller is further configured to control the thermal treatment device to heat the basin and any contents therein based on weight measurement information received from the weight measurement device and temperature measurement information received from the temperature sensor to heat any contents in the basin to the target temperature.

In an additional example, a weight measurement device is described that includes a base and a reservoir supported by the base. The reservoir is configured to receive and hold a material to be weighed. The reservoir includes a base and a sloped sidewall extending vertically upwardly away from the base, with the base and sloped sidewall collectively forming a bounded cavity with open top surface that receives and holds the material to be weighed. The device also includes a weighing device positioned to obtain weight information concerning a weight of the reservoir and any contents therein, a user interface, and a controller. The controller is configured to receive weight measurement information from the weight measurement device concerning the weight of the reservoir and the material to be weighed therein and to display a weight of the material to be weighed on the user interface.

The details of one or more examples are set forth in the accompanying drawings and the description below. Other features, objects, and advantages will be apparent from the description and drawings, and from the claims.

BRIEF DESCRIPTION OF DRAWINGS

FIG. 12 is an exploded cross-sectional view taken along the A-A sectional line indicated on FIG. 1 showing an example arrangement of components.

DETAILED DESCRIPTION

Figure 1:
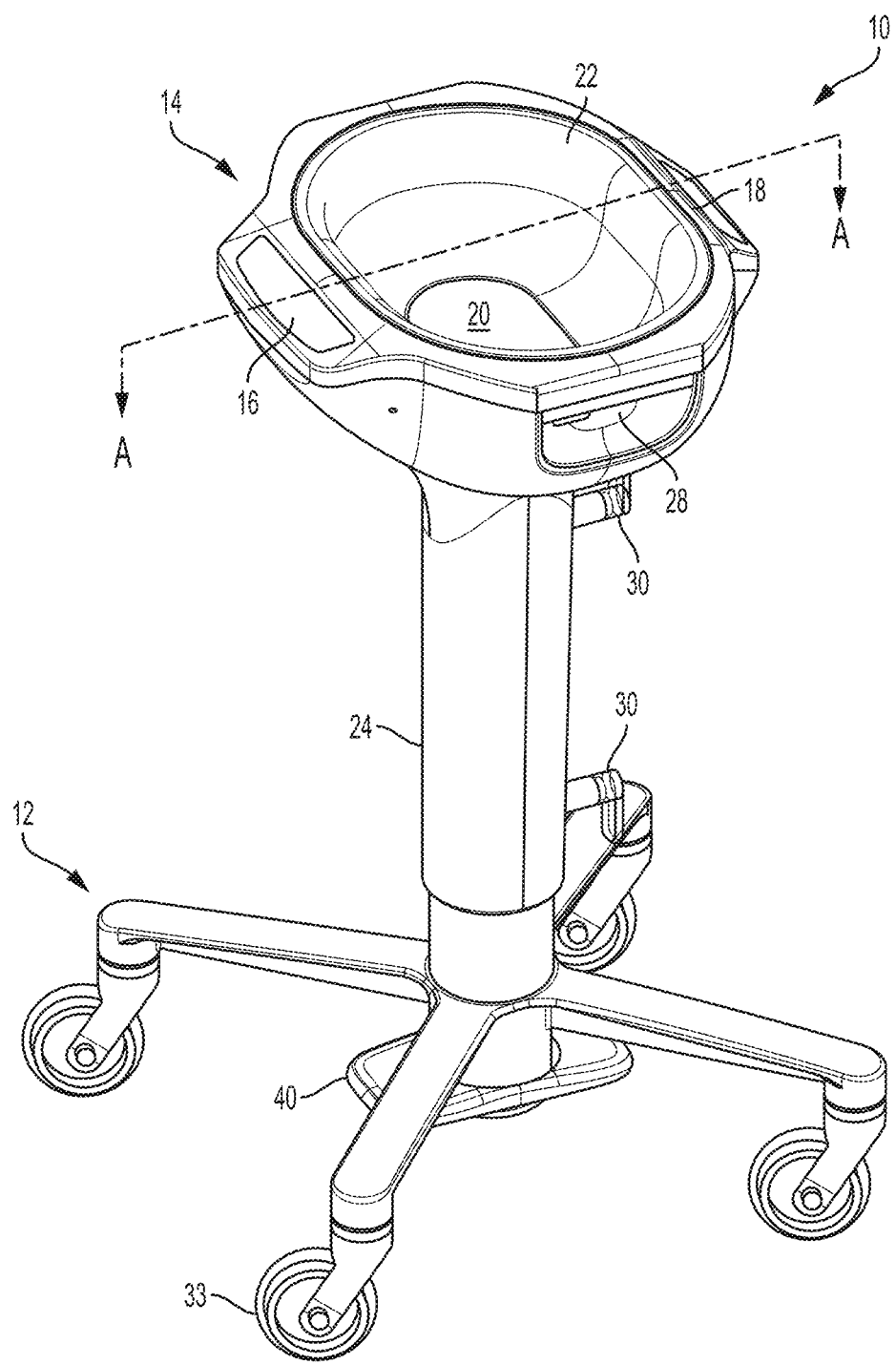
FIGS. 1-3 are perspective, side, and top views, respectively, of an example system for thermally treating a surgical fluid.

In general, this disclosure is directed to devices, systems, and techniques for monitoring and/or determining the amount of a material in a surgical environment and, optionally, adjusting the temperature of such material. In some examples, a system is configured for thermally treating surgical fluid before utilizing the fluid during a medical procedure. The surgical fluid may be temperature adjusted within the system to raise the temperature above ambient temperature or reduce the temperature below ambient temperature. The system can also maintain the surgical fluid at an elevated or reduced temperature relative to ambient temperature until the surgical fluid is ready to be used during a procedure. In use, the surgical fluid may be withdrawn from the system and dispensed over a surgical site on or in a patient to irrigate the site and flush away bodily matter. A suction device may be used to draw the surgical fluid back out of the patient along with flushed bodily matter, preventing the surgical fluid from accumulating in an open cavity of the patient.

In some examples, a thermal treatment system according to the disclosure monitors the amount of surgical fluid withdrawn from the system. By assuming that all the withdrawn surgical fluid not returned to the system is introduced into the patient, the system can indicate the amount of surgical fluid introduced into the patient during a procedure. In some configurations, the system includes a display that updates in substantially real-time and reports the volume of fluid withdrawn from the system. This information can be helpful to guide clinicians performing a procedure. For example, with knowledge of the amount of fluid introduced into the patient during the procedure, the clinician may confirm that a proportional (e.g., equal) amount of fluid has been withdrawn from the patient and collected using a suction device. As another example, the clinician may determine that the patient is being over irrigated based on the amount of surgical fluid consumed and slow or stop further irrigation.

A thermal treatment system according to the disclosure can include additional or different features to provide safe and efficient surgical fluid temperature adjustment. For example, a thermal treatment system may include a reader operable to read information encoded on a drape inserted into system. The reader may be implemented using a non-contact reader, such as an optical reader, RFID reader, NFC reader, or similar non-contact reader. The reader may read information encoded on or embedded in a drape inserted into the system. If the reader does not detect encoded information on the drape, or if the authenticity of the encoded information cannot be confirmed, the system may prohibit operation of a thermal treatment device. This can help ensure that if the material the drape is manufactured from is not compatible with the operating conditions of the system (e.g., temperature conditions), the system will not proceed with operation. As another example, the reader may detect if a drape has already been used based on the information read from the drape (e.g., and comparison to stored information identifying previously used drapes) and prevent the system from operating if the drape has already been used (and therefore likely is not sterile).

Figure 2:
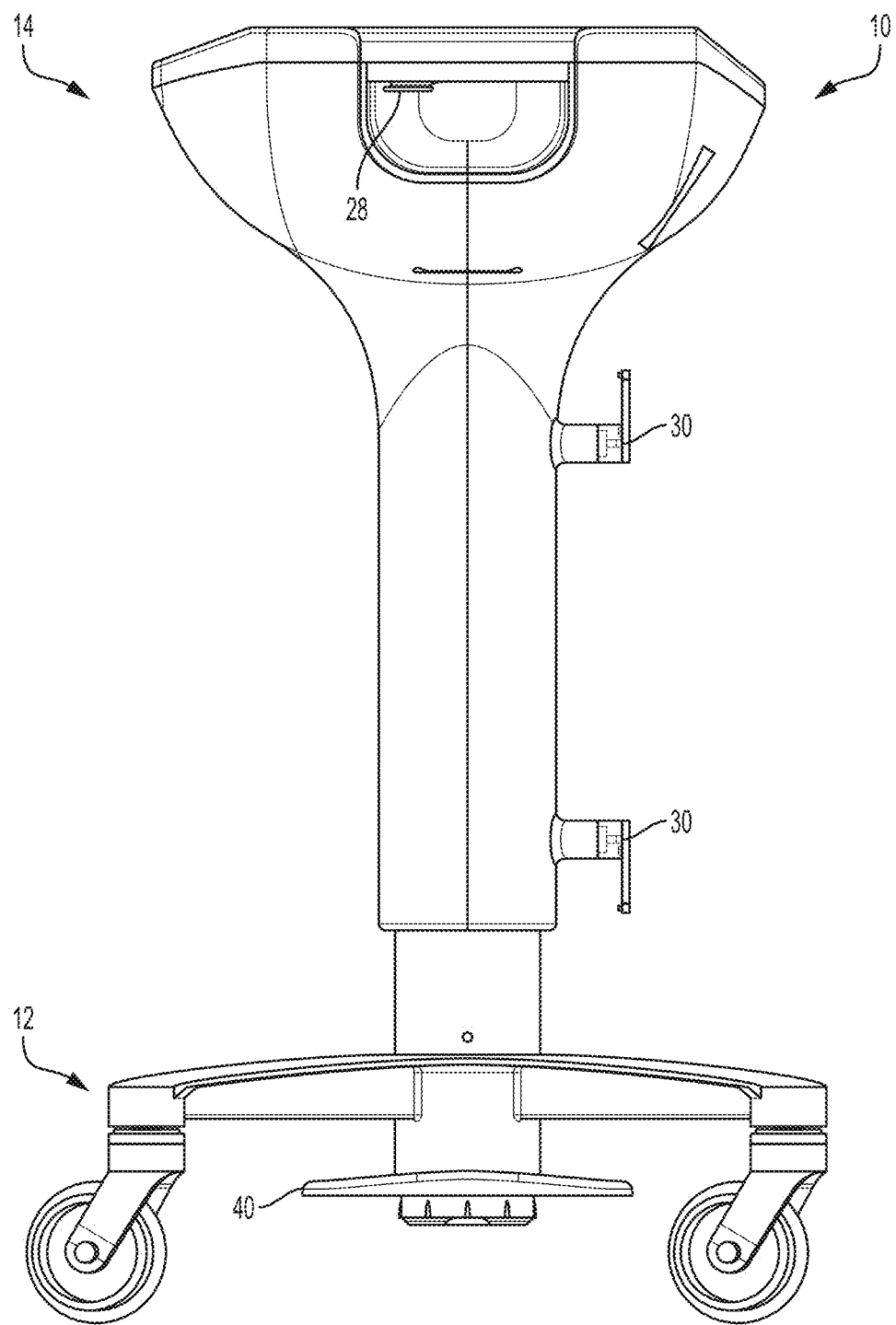
Figure 3:
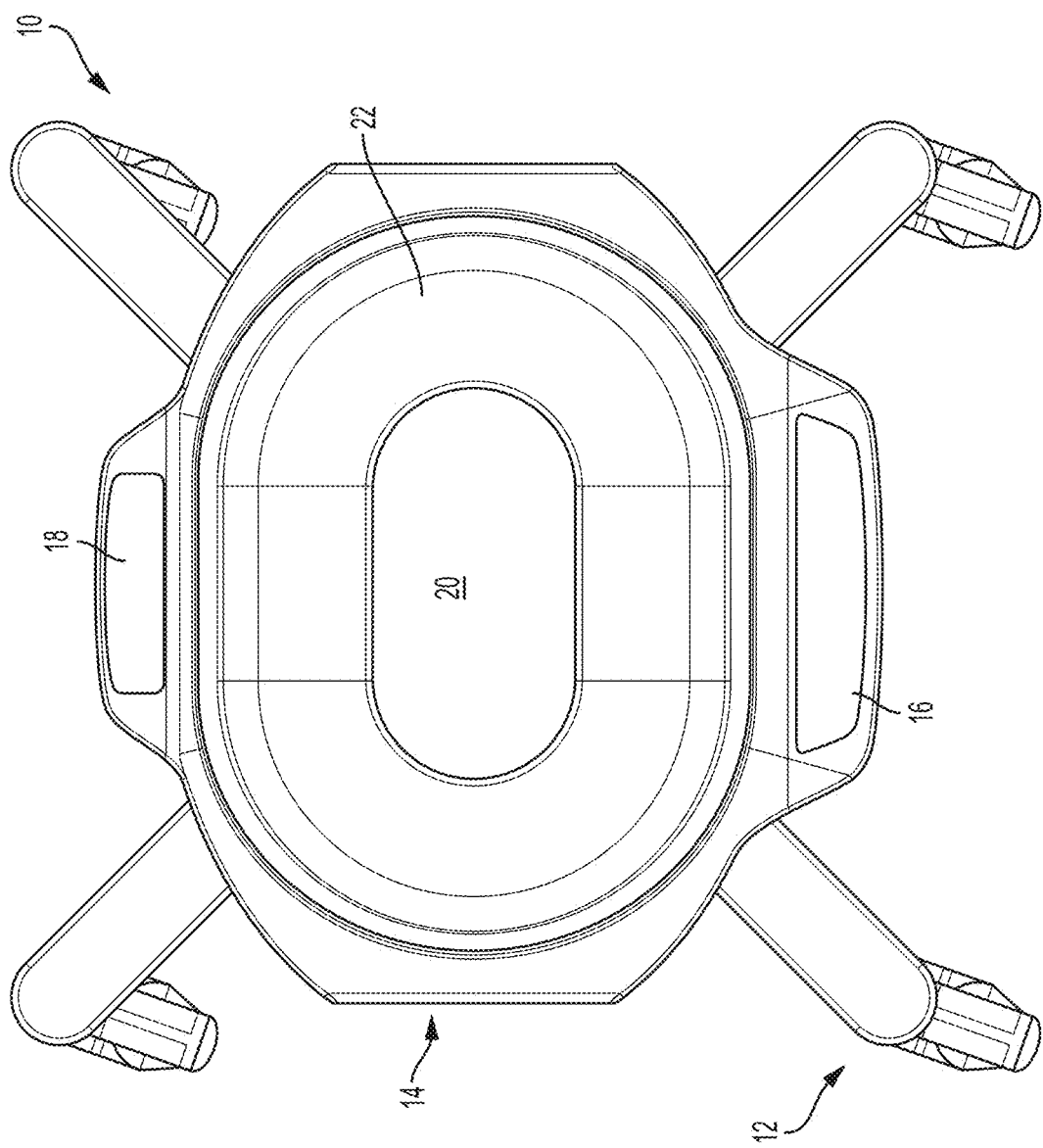

FIGS. 1-3 are perspective, side, and top views, respectively, of an example system 10 for thermally treating a surgical fluid. In the illustrated example, system 10 includes a base 12 and a basin 14. Basin 14 is supported by and vertically elevated above base 12. Basin 14 may provide an open reservoir into which surgical fluid can be dispensed or other material being processed introduced. Once added to basin 14, the surgical fluid can be temperature adjusted within the basin. For example, basin 14 may be thermally coupled to a thermal treatment device that can raise or lower the temperature of thermal fluid. Basin 14 can also maintain surgical fluid at a target temperature until the fluid is removed from the basin and used in the procedure.

As described in greater detail below, system 10 may monitor the amount of fluid added to and/or removed from basin 14. System 10 may, but need not, also receive indications when non-fluid components, such as medical tools, are added to and/or removed from basin 14. During a procedure, a clinician may add fresh surgical fluid to basin 14 and also place one or more medical tools in the basin. The terms fresh surgical fluid or fresh material indicates that the fluid or material is being introduced to basin 14 for the first time (e.g., from a sterile container) and is not fluid or other material that has been withdrawn from the basin and is being reintroduced back to the basin. The medical tools may be surgical instruments that are kept at a controlled temperature before being taken out of basin 14 and inserted into the patient. Additionally or alternatively, the medical tools may be equipment for delivering surgical fluid from basin 14 to the patient, such as an asepto bulb syringe and/or a graduated measuring container.

System 10 can determine when surgical fluid is removed from basin 14 and distinguish from when medical tools are removed from the basin. System 10 may also identify when fresh fluid is added to basin 14 and distinguish from when medical tools are added to the basin. System 10 may then determine the amount of surgical fluid removed from basin 14 during a procedure based on the amount of fluid added to the basin and the current volume of surgical fluid in the basin. System 10 may further determine when one or more medical tools have been added and/or removed from the basin to determine the amount of surgical fluid removed from the basin.

To allow an operator to interact with system 10 and control different settings, system 10 may include a user interface. In the example of FIGS. 1-3, system 10 includes at least one user interface 16. User interface 16 can include a user input through which a clinician inputs information to system 10 and a user output from which the clinician receives information from the system. For example, user interface 16 may include one or more manipulable inputs that the clinician can interact with to adjust settings of system 10, provide an indication that fresh fluid is being added to basin 14, provide an indication that non-surgical components are being added or removed from system 10, or the like. The manipulable user input may be implemented as physically depressible buttons (e.g., switches), portions of a touch screen that a clinician can interact with, or other features that a clinician can interact with to convey information to system 10. The user output of user interface 16 may be a display that provides graphical and/or textual information concerning the operation of system 10.

While user interface 16 is illustrated as including a display and one or more buttons that a user physically touches to interact with system 10, the system may include any type of interface that a user may interact with to communicate with the system. For example, system 10 may include a microphone that detects sounds (e.g., fluid being poured into basin 14) and/or audible commands from the user. As another example, system 10 may include an optical detector that detects user action (e.g., fluid being poured into basin 14, a tool being removed from the basin) and/or a non-contact user command (e.g., a user gesture such as placing a hand or fluid bottle in front of an optical sensor). When implemented with optical detection capabilities, the system may include a camera that monitors basin 14 and/or the surrounding space and performs image recognition techniques to detect user interaction and/or commands with the system. As another example, the system may include a light emitter that detects when a light pathway is broken, such as a laser beam over the opening of basin 14 to detect when material is are added and/or removed from the basin. In this configuration, the system may determine whether surgical fluid or a medical tool is being added or removed from basin 14 based on the optical reflection characteristics and material properties of the component being added or removed. System 10 can include multiple different types of user interfaces (e.g., physical touch, audible, optical) any one of which can be engaged by the user to allow the system to determine information about the content of what is being added or removed from the system.

Additionally, while system 10 in FIG. 1 shows user interface as having a display physically mounted on basin 14, it should be appreciated that the display need not be physically attached to the system and/or the system may not have a display. For example, system 10 may include a remote electronic device (e.g., computer, tablet, smart phone, touch screen monitor) that is physically separate from basin 14 but in wireless communication with the basin, either directly or indirectly. A user may interact with the remote electronic device to input parameters for controlling basin 14 (e.g., a target temperature to which fluid is to be heated) and/or may receive data from the basin (e.g., data indicating a volume of fluid added and/or removed from the basin, a weight of material in the basin, a set temperature and/or a current temperature for material in the basin).

In addition to or in lieu of having a remote user interface 16 through which a user can interact with basin 14, the basin may be configured to transfer data related to its use to a remote computer. For example, basin 14 may transfer data concerning one or more of: a target temperature to which the basin was set during a procedure, the amount of fluid added to the basin during the procedure, the amount of fluid removed from the basin during the procedure, the times at which one or more medical tools were added and/or removed from the basin, the actual temperature of the fluid in the basin throughout the procedure and/or as fluid was removed from the basin, and combinations thereof. The basin 14 may transfer the data to a remote computer through a removable non-transitory storage medium (e.g., flash drive, CD), through a wired connection, and/or through a wireless connection (e.g., cellular telephone protocol, Bluetooth™ protocol, Wi-Fi protocol, or other radio frequency). In some examples, basin 14 transfers the data to a cloud computing network. The transferred data may include or be associated with a patient identification corresponding to a patient for whom system 10 was used during a medical procedure. Using one or more remote computers, the data from a single procedure or aggregated data from multiple procedures may be analyzed to identify trends and utilization improvement opportunities, e.g., for a specific device or for multiple devices within a common ownership structure.

In applications where system 10 includes a display, the system can be configured with a single display or multiple displays. In FIGS. 1-3, system 10 is illustrated as having a first display that forms part of user interface 16 and a second display 18. The first display is positioned on an exterior surface of one side of basin 14 while the second display is positioned on an exterior surface on a substantially opposite side of the basin. This arrangement can be useful to allow clinicians working on different sides of basin 14 to see information regarding the operation of system 10. In some examples, second display 18 is part of a user interface that includes the same features and functionalities (e.g., user input(s) and/or user output(s)) as first user interface 16. This can allow the clinician to present information to and receive information from system 10 when working on either side of the system. In other examples, second display 18 may be a display that provide a user output but does not have user input controls. In these applications, the clinician may enter information or commands through user input(s) on user interface 16 but be able to view output information on both displays. Example user interface and display configurations that can be used as user interface 16 and/or display 18 are described with respect to FIGS. 8A and 8B.

In addition, although the first display forming part of user interface 16 and the second display 18 are shown being mounted at a downwardly directed angle with respect to uppermost edge of basin 14, the displays can be mounted at any desired angle. For example, the first display forming part of user interface 16 and the second display 18 may be mounted at the same angle or different angles with respect to the basin. In one example, second display 18 is mounted on the system at a sharper angle (e.g., such that the display is more perpendicular with ground) than the first display, providing greater visibility to users positioned farther away from the basin. Moreover, while the first display forming part of user interface 16 and the second display 18 are shown on opposed exterior surfaces of basin 14, one or both of the displays may be remote from the basin and communicatively coupled thereto (e.g., to display information associated with the basin although not physically connected thereto), as discussed above. For example, first display forming part of user interface 16 and/or the second display 18 may be implemented using a television or computer monitor (e.g., within an operating suite), on a portable device carried by a clinician (e.g., mobile phone, tablet computer), or otherwise located physically separate from basin 14.

Thermal treatment system 10 includes basin 14. Basin 14 provides a reservoir that receives and holds surgical fluid. In general, basin 14 can define any polygonal (e.g., rectangle, square, hexagonal) or arcuate (e.g., circular, elliptical) shape, or even combinations of polygonal and arcuate shapes. In the illustrated example, basin 14 is shown as a general oval shape and includes a base 20 and at least one slope sidewall 22 extending vertically upwardly away from the base. Base 20 and sloped sidewall 22 collectively form a bounded cavity with open top surface that receives and holds the surgical fluid. Configuring basin 14 with sloped sidewall(s) instead of straight sidewalls helps prevent surgical fluid from accumulating in corners where the sidewall(s) intersects the base. That being said, in other examples, basin 14 may be formed with straight sidewalls. Further, while basin 14 is illustrated as having an open top surface for adding material to the basin and withdrawing material from the basin, the basin may be closed over its top surface in other configurations.

In addition, although basin 14 is illustrated as having a single reservoir for holding medical fluid, the basin may be formed with multiple reservoirs separated from each other. For example, basin 14 may be a single cavity with internal partition(s) or divider(s) separating one or more reservoir cavities from fluid communication with one or more other reservoir cavities. Alternatively, basin 14 may be configured with multiple cavities (e.g., each separately molded or formed), each providing a separate reservoir for receiving and holding fluid. In use, each cavity may be filled with the same fluid, or at least one cavity may be filled with a fluid different than the fluid filled in at least one other cavity. Additionally, in some configurations, each cavity may be provided with a separate thermal treatment device, allowing independent temperature adjustment of different cavities. This can be useful, for example, to heat fluid in different cavities to different temperatures, heat fluid in one cavity while chilling fluid in another cavity to create a slush, or otherwise providing temperature control flexibility.

Any type of material may be introduced into and removed from basin 14 during a procedure, including any type of surgical fluid during a medical procedure. Example types of medical fluid that may be used during a medical procedure include water, saline, or the like. The surgical fluid may or may not include medicament, such as compounds imparting antibacterial properties, anticoagulation/coagulation properties, anesthesia properties, or the like. Alternative materials that may be introduced into basin 14 can include a medical specimen extracted from a patient for weighing (e.g., in embodiments in which basin is configured to measure weight), blood, platelets, or materials for thermal adjustment before being introduced into a patient, or non-medical related materials (e.g., in applications in which system 10 is not used in a medical environment).

Figure 9A:
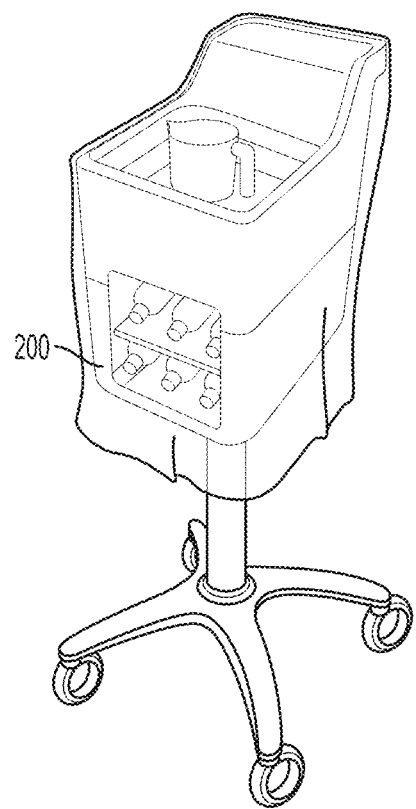
FIGS. 9A and 9B illustrate example bottle pocket configurations that can be used on the example system of FIGS. 1-3.
Figure 9B:
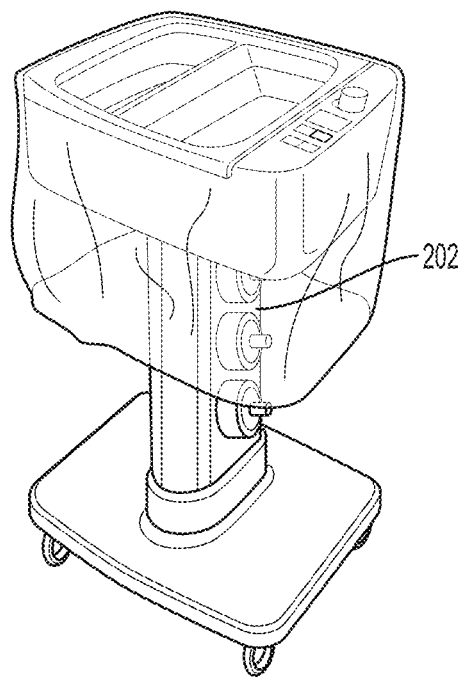

In the configuration of FIGS. 1-3, basin 14 is supported by and vertically elevated above base 12. In particular, basin 14 is mounted on an elongated housing 24 that extends vertically upwardly from base 12. Base 12 and housing 24 can elevate basin 14 to a position where it is convenient for a clinician to interact with the basin. In some examples, housing 24 contains one or more receiving cavities that are configured to receive containers of surgical fluid. For example, housing 24 may contain one or more pockets positioned along the length of the housing into which surgical fluid containers can be inserted. The pockets may or may not be heated to provide pre-warmed surgical fluid. In either case, the pockets may store container(s) of surgical fluid for ready access during a medical procedure. If additional surgical fluid is needed during the procedure, the clinician can extract a container of fresh surgical fluid from the pocket in housing 24 and add the surgical fluid to basin 14. For example, FIG. 9A illustrates a thermal treatment system having a bottle pocket 200 formed in the housing defining basin 14. FIG. 9B illustrates another thermal treatment system having a bottle pocket 202 formed along the length of the housing. Such bottle pocket designs can be used on thermal treatment system 10 of FIGS. 1-3.

Figure 4A:
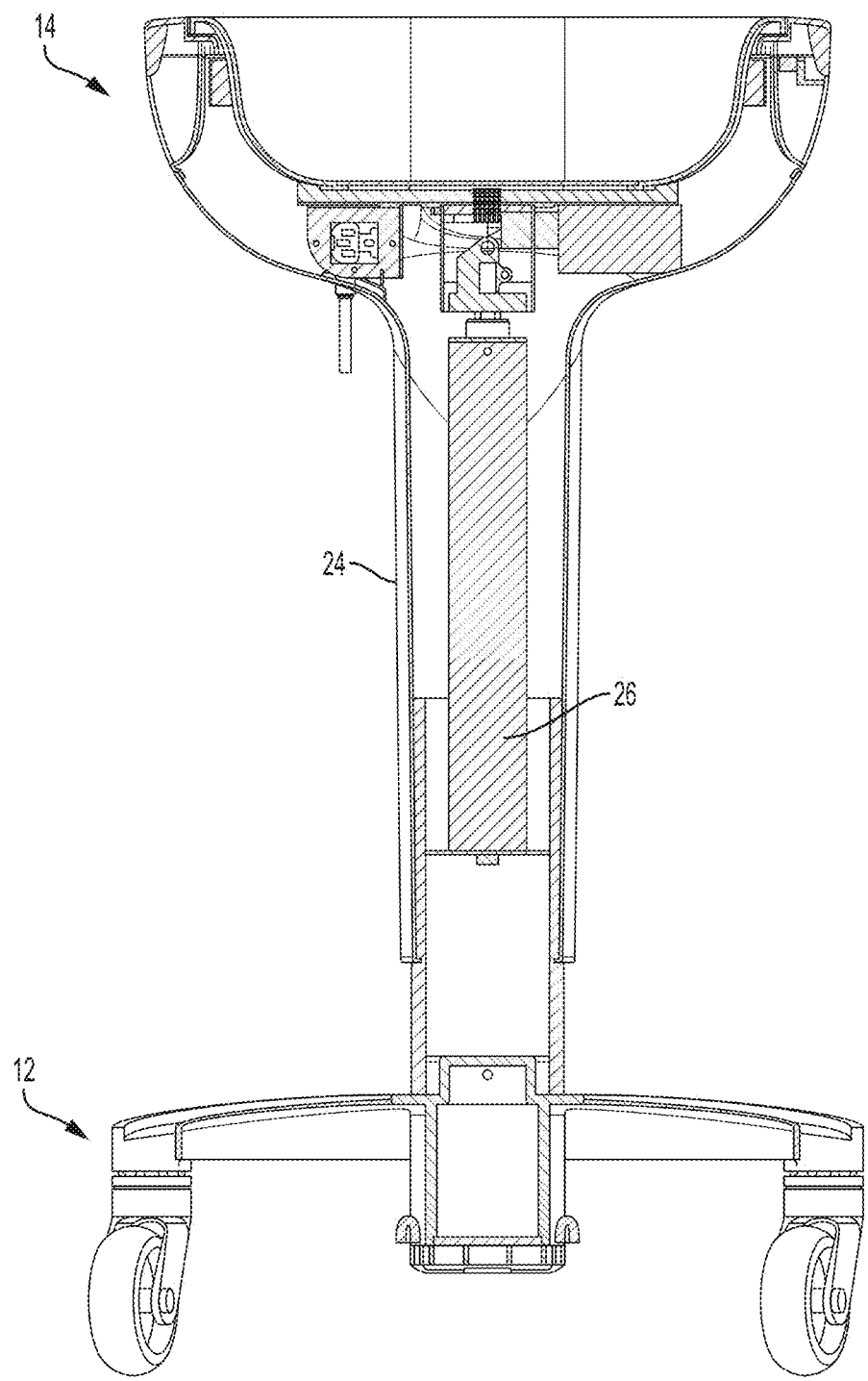
FIG. 4A is a sectional view of the example system of FIGS. 1-3 taken along the A-A sectional line indicated on FIG. 1.

In some examples, basin 14 is at a fixed height relative to base 12 and/or the surface (e.g., floor, counter, table top) on which system 10 is mounted. In other examples, system 10 includes a height adjustment mechanism that is operable to adjust a height of basin 14 relative to base 12. This can be useful to allow clinicians of different heights to reposition basin 14 at a comfortable working height. FIG. 4A is a sectional view of system 10 from FIG. 1 taken along the A-A sectional line indicated on FIG. 1 showing an example height adjustment mechanism.

As shown in the example of FIG. 4A, system 10 includes a height adjustment mechanism that is implemented with a piston 26 and an adjustment lever 28 (FIG. 1). Piston 26 may include a sliding shaft positioned in a chamber containing a compressible fluid (e.g., gas, liquid) or a spring. The sliding shaft can be moved by fluid or spring pressure to raise basin 14, and an operator can push basin 14 downwardly to lower the basin and cause the sliding shaft to move against fluid pressure or the spring. Adjustment lever 28 can control the position of piston 26 and, correspondingly, the position of basin 14. For example, adjustment lever 28 may open and close a valve that controls fluid movement to piston 26 and/or move a detent into and out of a locking aperture. Adjustment lever 28 can be positioned as a hand control as shown in FIG. 1 or may be implemented as a foot control. In other configurations in which system 10 has a height adjustment mechanism, the height adjustment mechanism may be implemented using a rotating locking collar that controls the position of two sliding shafts relative to each other.

Mounting basin 14 to be movable via a height adjustment mechanism may be useful to enable the basin to be moved to different elevations, e.g., depending on the height of the operator using the basin and space constraints in the environment in which the basin is being used. In practice, in applications in which basin 14 is mounted above a piston 26, the basin may rotate in the horizontal plane unless otherwise constrained. Such constraint may come from the configuration of piston 26 having a limited range of rotation. However, when basin 14 is at an elevated height, fluid present in the basin may cause the center of gravity to shift and the basin may have a tendency to rock or wobble in the horizontal plane undesirably. Such rocking or wobbling may cause fluid present in basin 14 to spill out of the basin if too severe. To help constrain basin 14 from unintended rotational movement, system 10 may include one or more anti-rotational features to help constrain the basin from rotating.

Figure 4B:
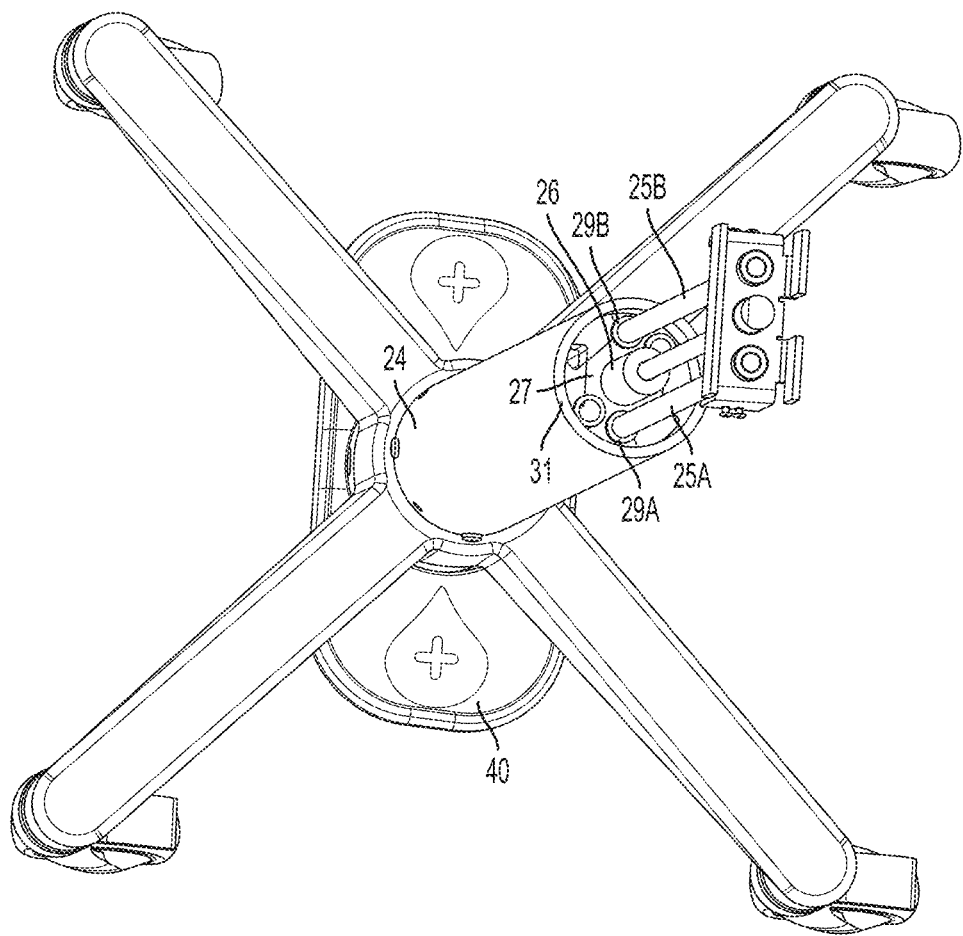
FIG. 4B is a perspective top view of the example system of FIG. 1 shown with the basin removed for purposes of illustrating an example configuration of a height adjustment mechanism.

FIG. 4B is a perspective top view of system 10 (shown with basin 14 removed for purposes of illustration) showing an example configuration of a height adjustment mechanism with an anti-rotation configuration. In this example, piston 26 is mounted within a central lumen of housing 24 between base 12 and basin 14. In addition, the height adjustment mechanism includes at least one anti-rotation rod, which is illustrated as being implemented using two anti-rotation rods 25A, 25B. The anti-rotation rods 25A, 25B extend parallel to piston 26 and are on different sides of the piston. The anti-rotation rods 25A, 25B can extend partially, and in some examples fully, along the length of housing 24 and can be raised and lowered with piston 26. For example, anti-rotation rods 25A, 25B may be fixedly connected at one end (e.g., at their upper ends to basin 14) and may travel through a fixed opposite member and/or be telescoping at their opposite ends. When so configured, anti-rotation rods 25A, 25B may raise and lower with basin 14 and piston 26 and may counteract a rotational moment applied to basin 14, reducing or eliminating any rotational movement of the basin.

In other configurations, the height adjustment mechanism may include two components movable relative to each other that are interlocked with a tongue and groove configuration. For example, housing 24 and/or piston 26 may include one member connected to base 12 and a second member connected to basin 14, with the two members being slidable relative to each other. Providing a slidable and interlocking tongue and groove connection between the two members can help minimize rotation of basin 14.

To accommodate various components positioned in housing 24 and/or extending from base 12 to basin 14, the lumen defined by housing 24 may include one or more openings through which components in the housing extend. In the example of FIG. 4B, housing 24 defines the first lumen 27 through which piston 26 is inserted, one or more secondary lumens 29A, 29B through which the one or more anti-rotation rods 25A, 25B are inserted, and an optional third lumen 31 through which wiring can be inserted. The third lumen 31 may be in the form of a wiring race that allows a communication cable to extend from basin 14 to the bottom of housing 24 and/or base 12.

For example, as discussed in greater detail below, system 10 may include a foot actuatable peddle 40. To send and/or receive signals between foot actuatable peddle 40 and basin 14 (e.g., a controller mounted in the basin housing), system 10 may include a communication cable (e.g., electrical cable, optical cable) extending from the foot actuatable peddle to the basin. The cable may have a length sufficient to reach from the foot actuatable peddle to the basin when the basin is at its maximum elevated position. The cable may have coils (e.g., such as a coiled telephone cord) to allow the cord to be extended and retraced as basin 14 is elevated and lowered. As another example, the cable may extend out of a retraction housing that causes the cable to be draw out of the housing and be retracted into the housing as basin is elevated and lowered, respectively. In either case, configuring housing 24 with a wiring lumen physically separated from a lumen housing piston 26 can be useful to prevent the cable from being pinched, kinked, or broken by piston 26 as basin 14 is raised and/or lowered. In some examples, the different lumens into which housing 24 is divided extend the length of housing 24. In other examples, housing 24 includes one or more divider plates to define the lumens while the space above and/or below the one or more divider plates are undivided.

Independent of the specific configuration of the height adjustment mechanism, the height adjustment mechanism may be designed to position the basin at an elevation ranging from 24 inches to 60 inches. For example, the height adjustment mechanism may allow an operator to adjust a top surface of basin 14 to any desired height, including heights within a range from 36 inches to 48 inches. The height adjustment mechanism (e.g., piston, when used) may provide a force effective to lift a weight of at least 5 kilograms, such as from 7 kilograms to 15 kilograms, over the entire range of travel.

Base 12 supports system 10, e.g., on a floor of a medical procedure room, on a table, on a countertop. In the configuration of FIGS. 1-3, base 12 is mounted on wheels 33 so as to be movable from one location to another. One or more of the wheels can be lockable to prevent base 12 from moving once positioned at a desired location. In other examples, base 12 does not include wheels 33. Moreover, while base 12 is illustrated as being physically separate from basin 14 and connected thereto via housing 24 and piston 26, in other examples, basin 14 and base 12 may be physically integrated together to form a unitary structure. It should be appreciated therefore that base 12 need not be a physically separate structure from basin 14 but may be a portion of the basin structure which rests on a support surface. Accordingly, base 12 need not be configured with outwardly extending spokes but may be any type of support structure that forms a base for basin 14. In some examples, system 10 may not include base 12.

To power system 10, including a thermal treatment device that controls the temperature of surgical fluid placed in basin 14, the system may have a power cord that plugs into mains/wall power. To manage the power cord when not in use, system 10 in FIGS. 1-3 includes a cord wrap structure. In particular, the illustrated system includes a pair of longitudinally spaced hooks 30 configured to receive a power cord wrapped thereabout. In other configurations, system 10 can include a spring-loaded retraction device that automatically retracts the power cord into a power cord retention chamber. In addition to or in lieu of using a power cord to supply wall power to system 10, the system may contain an internal battery to power the functions of the system. When so configured, one or more internal batteries may be provided that may or may not be rechargeable and/or replaceable. When used, the battery can be the primary power source for powering system 10 or, instead, may function as a backup power source in the event in that the main power source (e.g., wall power) fails.

Since system 10 may be deployed to different geographical regions throughout the world, the system may include circuitry to run on different power sources. For example, the system may operate on 110 volt electricity in some countries and 220 volt electricity in other countries. To configure system 10 as a universal device that can run on any voltage that may be provided from a wall socket in the local country where the system may be deployed, the system may include appropriate electrical circuitry. In some examples, system 10 includes a transformer that steps that voltage received from the wall socket up or down to an appropriate voltage for operating system 10, e.g., including a thermal treatment device therein. In other examples, system 10 may include a voltage sense integrated circuit that detects the voltage from the wall socket to which the device is connected and provides a control signal for controlling electrical operation of the device. The control signal from the integrated circuit may cause one or more electrical pathways to open or close. For example, when the integrated circuit detects a high voltage (e.g., 220 V), electricity may be supplied in parallel electric pathways to the thermal treatment device. By contrast, when the integrated circuit detects a lower voltage (e.g., 110 V), electricity may be supplied in a series electrical pathway to the thermal treatment device. Accordingly, system 10 and the thermal treatment device therein can operate on any voltage supplied without requiring or including a transformer. The absences of a transformer can substantially reduce the weight of system as compared to when a transformer is included.

In use, a clinician may dispense fresh, sterile surgical fluid into basin 14 in preparation for subsequently using the surgical fluid in a medical procedure. While surgical fluid may be dispensed directly into basin 14, the clinician may instead insert a sterile drape into basin 14 before dispensing the surgical fluid into the draped basin. The sterile drape may be a disposable liner that creates a sterile field which surgical fluid and other sterile medical components can contact. The drape can separate the sterile field from a non-sterile field.

When used, the disposable drape may be made from a material that is impervious to surgical fluid and sufficiently flexible to conform to the walls of basin 14. The drape can be fitted or non-fitted. A fitted drape can be constructed such that the drape is formed to the contour of basin 14 (e.g., matches the size and/or shape of the basin). A non-fitted drape may be a flat or pleated and have a length sufficient to be placed over basin 14. In either case, the drape may be placed in basin 14 so as to conform to the walls of the basin. In some examples, the drape also extends over the sides of basin 14, e.g., hanging down parallel to housing 24. Additionally, in some examples, the drape may have internal partition(s) or divider(s) creating one or more reservoir cavities that are separated from fluid communication with one or more other reservoir cavities. When so configured, the drape can transform a single fluid cavity of basin 14 into multiple fluid cavities.

A disposable drape used with basin 14 may have a thickness sufficient to resist tearing and puncturing during normal use but also be sufficiently thin to allow efficient thermal transfer through the drape. While a disposable drape can be made from any suitable materials, in some examples, the drape is made from a polymeric material (e.g., polyethylene, polypropylene, polystyrene, polyurethane). The drape (or a portion thereof) may be transparent or translucent to allow an operator to see features covered by the drape.

In one particular application, a disposable drape used with system 10 and basin 14 is a thermoformed polymeric drape. A thermoformed drape can be formed by heating a plastic sheet to a temperature where the plastic sheet becomes pliable and then conforming the plastic sheet to a mold that has the dimensions (e.g., size and shape) of basin 14. Upon cooling, the thermoformed drape will retain the shape of the mold and, correspondingly, basin 14. Depending on the thickness of the plastic sheet used, the resulting thermoformed drape may be rigid or semi-rigid. For example, a semi-rigid drape may maintain the size and shape profile of basin 14 but have flex that allows the drape the bend and flex. A thermoformed drape may appear stronger and more robust to a clinician than a simple flexible plastic sheet drape and therefore may be desired because of apparent resistance to puncturing.

As briefly mentioned above, a drape used with system 10 may contain machine readable information that identifies the drape. When the drape is placed on basin 14, the machine-readable information can be read by a reader of system 10 to determine if the drape is suitable for use with the system. This can prevent improper drapes, such as drapes that do not have the appropriate strength or thermal resistance characteristics, from being used on system 10. For example, the drape may contain information that can be read by an optical or electro-magnetic reader to determine if the drape is authorized for use with system 10.

In some configurations in accordance with this example, the drape contains a tag encoding machine-readable information. The tag may be adhered to a surface of the drape or embedded within the drape (e.g., sealed between different layers of polymeric material). The tag can contain information identifying the drape, such as a code or manufacturing number (e.g., lot or unit number), the name of the manufacturer, the date of manufacture, and the like. In some configurations, the tag is configured as a non-contact tag whose information can be read by bringing the tag in proximity to a reader of system 10 without requiring the tag physically contact the reader. This can be helpful to allow a clinician to position the tag in close proximity to a corresponding reader simply by inserting the drape in basin 14 without requiring further placement of the tag. Although any type of tag suitable for use with a non-contact reader can be used, in some examples, a drape used with system 10 contains a radio frequency identification (RFID) tag or a near field communication (NFC) tag.

Figure 5:
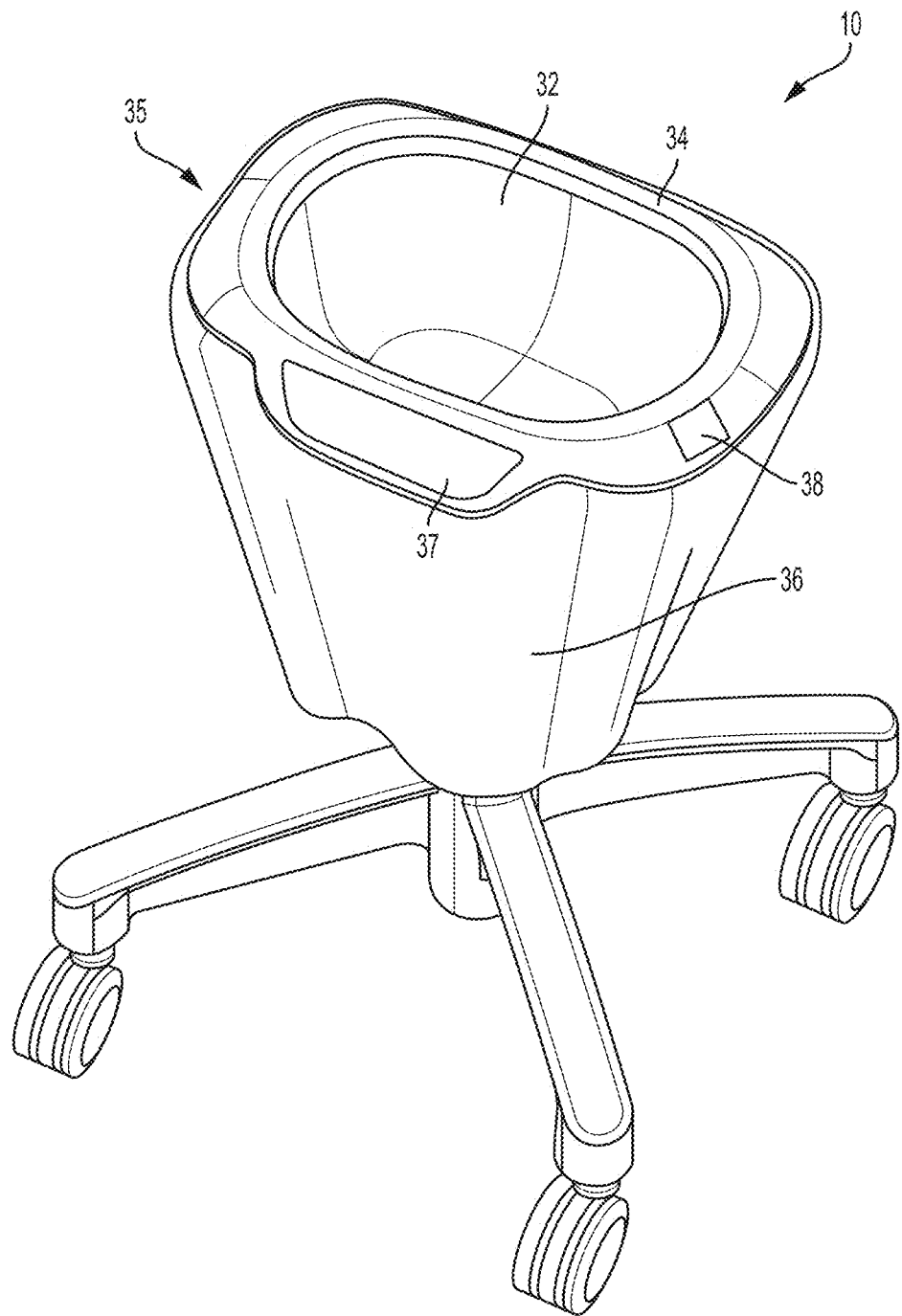
FIG. 5 is an illustration of an example drape that can be used with the system of FIGS. 1-3.

FIG. 5 is an illustration of an example drape 35 that can be used with system 10 in FIGS. 1-3. In the illustrated example, drape 35 includes a rigid or semi-rigid bowl portion 32 that is inserted into basin 14 and conforms to the size and shape of the basin. Bowl portion 32 has a rim 34 that extends around and over at least a portion of the edge of basin 14, e.g., allowing the drape to snap or lock on the rim of the basin. In different examples, rim 34 may be friction fit on the edge of basin 14 or may include mechanical engagement features that lock on/into the edge of the basin, preventing drape 35 from inadvertently dislodging from basin 14. To allow a clinician to view and interact with system 10, drape 35 may include physical cutouts or transparent windows 37 that are configured to be positioned over user interface 16 and display 18.

In addition, in the example of FIG. 5, drape 35 further includes a skirt 36 and a tag 38 containing information identifying drape 35. Skirt 36 is connected to rim 34 and hangs down over the edge of basin 14. Skirt 36 may be formed of a flexible material, such as flexible plastic that is bonded to a thermoformed bowl portion 32. Tag 38 can contain machine-readable information (e.g., encoded on a computer readable memory that is part of tag 38). Tag 38 is positioned on drape 35 such that, when the drape is placed on basin 14, the tag is in close enough proximity to have its information read by a corresponding reader of system 10. While FIG. 5 illustrates one example configuration of a drape according to the disclosure, other configurations of drapes can be used as described herein, and it should be appreciated that the disclosure is not limited in this respect.

With further reference to system 10 in FIGS. 1-3, the example thermal treatment device includes a foot actuatable peddle 40. Generally, medical procedures are performed in an operating room or other medical facility with the assistance of various sterile and non-sterile medical personnel. The sterile personnel refers to personnel that have taken the necessary precautions enabling them to interact with objects in a sterile field without contaminating that field, while non-sterile personnel refers to personnel that have not taken those precautions and are capable of contaminating the sterile field. Since thermal treatment system 10 treats a sterile surgical fluid in the sterile field during a medical procedure, sterile personal are generally needed to operate the system.

Configuring thermal treatment system 10 with foot actuatable peddle 40 can be useful to provide an alternative mechanism for interacting with the system. In some examples, foot actuatable peddle 40 may function as a user input that can be used by a clinician in addition to or in lieu of user interface 16 to input information into system 10. For example, a clinician may press on foot actuatable peddle 40 to provide an indication to system 10 that fresh fluid is being added to basin 14, that non-surgical components are being added or removed from system 10, or the like. Depending on the configuration of system 10, foot actuatable peddle 40 may provide an alternative input for conveying information to the system that can also be performed using user interface 16 as discussed above. In other configurations, foot actuatable peddle 40 may be used to convey information to system 10 that cannot be provided through user interface 16.

Actuation of peddle 40 (e.g., pressing the peddle downwardly or pulling the peddle upwardly with a foot) can convey information to system 10 without requiring the clinician to use their hand to interact with user interface 16 (in instances in which user interface 16 is configured to receive input via physical touching from a user). Configuring system 10 with foot actuatable peddle 40 can be useful for a variety of reasons. For example, sterile personnel may not be able to engage user interface 16 because their hands are occupied. In these situations, the sterile personnel may engage foot actuatable peddle 40 to interact with system 10. As another example, non-sterile personnel may be tasked with interacting with system 10, e.g., adding fresh surgical fluid to basin 14. Because these non-sterile personnel have not undergone necessarily sterilization protocols, they may not be allowed to interact with features in the sterile field, including user interface 16. However, because foot actuatable peddle 40 can be in the non-sterile field (e.g., outside of drape 35), non-sterile personnel may interact with system 10 using the peddle. For example, when adding fresh surgical fluid to basin 14, personnel may press on foot actuatable pedal 40 a first time to indicate that the surgical fluid is to be added to the basin. After adding the surgical fluid to basin 14, the personnel may press foot actuatable pedal 40 a second time to indicate that the surgical fluid has been added to the basin.

While peddle 40 is described as being actuatable, the entire peddle need not move or actuate to be considered a foot actuatable peddle. For example, peddle 40 may have a transducer or other switch, a portion of which moves in response to an operator physically pressing on peddle 40. The external portion of peddle 40 which the operator's foot contacts may or may not move. In either case, peddle 40 may send a control signal to a controller of system 10 in response to the operator pressing on peddle 40.

Figure 6:
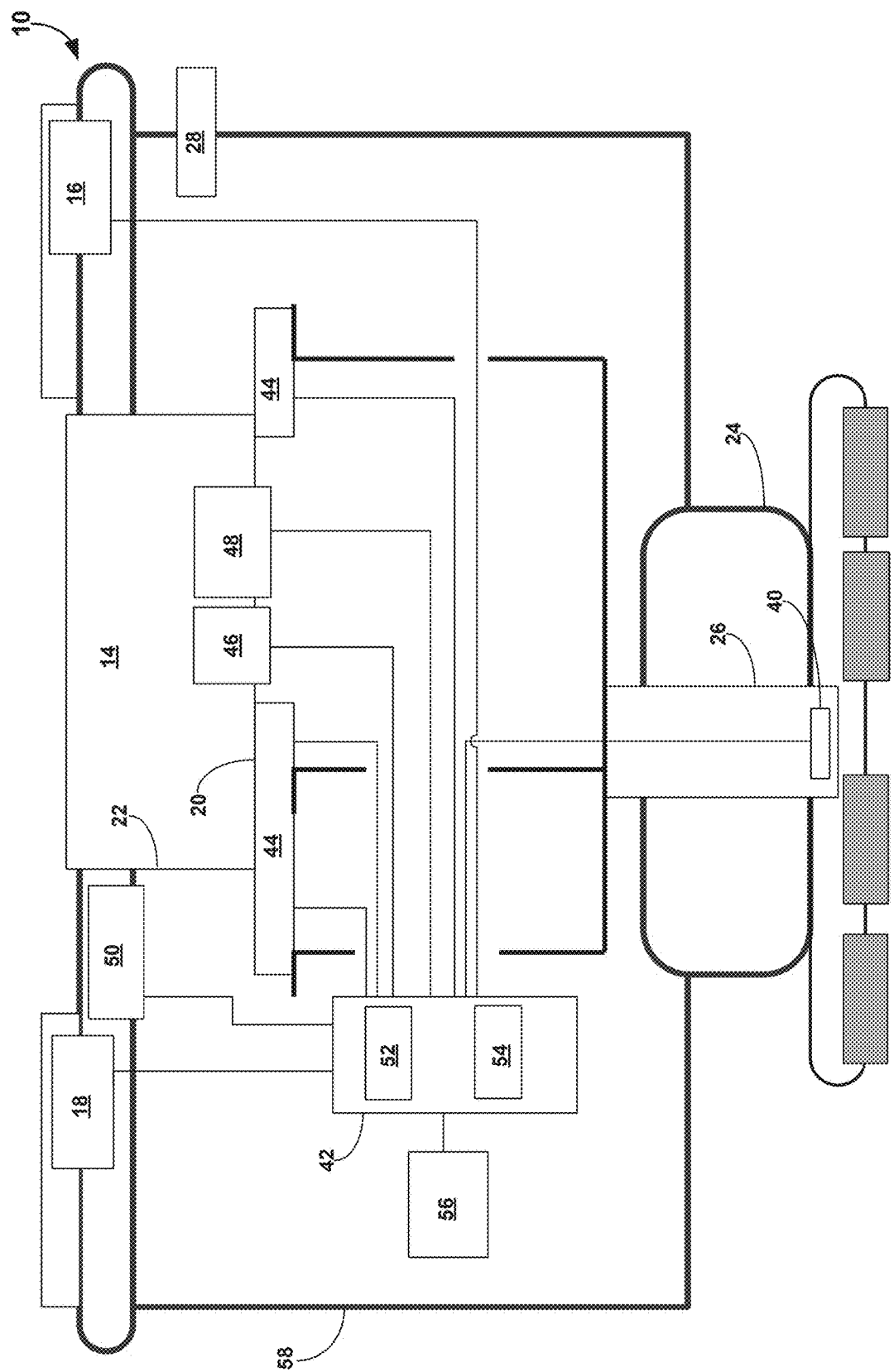
FIG. 6 is a functional block diagram illustrating components that can be used in the example system of FIGS. 1-3.

FIG. 6 is a functional block diagram illustrating components of an example configuration of thermal treatment system 10, which includes previously described base 12, basin 14, user interface 16, and display 18. System 10 in the illustrated example also includes a controller 42, volume measurement device 44, thermal treatment device 46, temperature sensor 48, and non-contact reader 50. Controller 42 is communicatively connected to user interface 16, display 18, foot actuatable pedal 40, volume measurement device 44, thermal treatment device 46, temperature sensor 48, and non-contact reader 50. Controller 42 can send communication signals to and/or receive communication signals from user interface 16, display 18, foot actuatable pedal 40, volume measurement device 44, thermal treatment device 46, temperature sensor 48, and non-contact reader 50 via wired or wireless connections, which in the example of FIG. 6 is illustrated as wired connections.

Controller 42 includes a processor 52 and memory 54. Memory 54 stores software for running controller 42 and may also store data generated or received by processor 52, e.g., from volume measurement device 44, temperature sensor 48, and non-contact reader 50. Processor 52 runs software stored in memory 54 to manage the operation of system 10.

System 10 in FIG. 6 also includes a power source 56 to deliver operating power to the various components of the system. Power source 56 may be a battery that is replaceable or rechargeable. Additionally or alternatively, power source 56 may be a power inlet that receives power from an external source. For example, power source 56 may be a power inlet connected to a cord that plugs into a wall socket to deliver power to system 10. The power received from the external source may recharge a battery contained in system 10 and/or power the various components of the system directly.

The various components of system 10 are illustrated as being contained within a housing or shell 58 that surrounds and defines basin 14. Housing or shell 58 can contain the various components of system 10 between the surfaces forming basin 14 and external wall surfaces of the housing. When so configured, the electrical components of system 10 illustrated in FIG. 6 may rise and lower with housing 58 when a height adjustment mechanism adjusts the vertical height of the basin 14. In other configurations, any or all of the electrical components illustrated in FIG. 6 may be housed in housing 24 and/or base 12.

During operation, controller 42 can control system 10 with the aid of instructions associated with information stored in memory 54 and with instructions received from an operator via user interface 16. Instructions executed by controller 42 may, for example, control thermal treatment device 46 to heat or cool surgical fluid in basin 14 to a target temperature set by an operator using user interface 16. Instructions executed by controller 42 may also determine the amount of surgical fluid removed from basin 14 during a medical procedure, for example based on feedback from volume measurement device 44, and control user interface 16 and/or display 18 to display a graphical and/or textual indication of the amount of fluid used during the procedure. In some examples, instructions executed by controller 42 determines if a drape (e.g., drape 35 from FIG. 5) placed on basin 14 is authorized to be used with system 10, for example based on feedback from non-contact reader 50, and further controls user interface 16 and/or display 18 to output an indication of whether or not the drape is authorized.

Controller 42 communicates with thermal treatment device 46 to control the temperature of surgical material placed in basin 14. Thermal treatment device 46 is thermally coupled to basin 14 and operable to adjust the temperature of the basin and any contents therein. Thermal treatment device 46 can be implemented using any device that produces a controllable temperature output. In some examples, thermal treatment device 46 can cool basin 14 and any contents therein (e.g., relative to ambient temperature) to produce a semi-frozen slush from surgical fluid placed in the basin. In other examples, thermal treatment device 46 can heat basin 14 and any contents therein (e.g., relative to ambient temperature) to produce a warmed surgical fluid.

When thermal treatment device 46 is implemented as a warming device, the thermal treatment device may generate heat via electrical resistance. The heat generated by electrical resistance can transfer into basin 14 and any contents therein by conduction, convection, and/or radiation. For example, wiring that generates heat via electrical resistance may be positioned in thermal and/or physical contact with basin 14, for example, within housing 58. Heat generated by thermal treatment device 46 can convey via conduction into basin 14 and any contents therein.

In other examples, a system 10 according to the disclosure does not include thermal treatment device 46. In these configurations, system 10 may be configured to track volume removed from basin 14 and/or provide weight measurements without thermally adjusting the contents in basin 14. For example, system 10 in such a configuration may provide a weight measurement device that can be utilized to measure the weight of various objects, such as a tissue sample extracted from a patient. System 10 may be configured with the features and functionalities described herein but without the thermal adjustment features and functionalities in such configurations.

As one example, thermal treatment device 46 may be a film heater positioned in thermal communication with basin 14. A film heater can be a thin film heater or a thick film heater. In a thin film heater, a layer of resistor material may be vacuum deposited on the surface of a substrate (e.g., flexible polymer sheet), after which a thin layer of conductive metal is deposited on top of the resistor material. Portions of the resulting film stack can be etched away to pattern of metal conductors. In a thick film heater, a paste that is a mixture of a binder, carrier, and metal oxides may be deposited on a substrate (e.g., printed on the substrate), and then fired in a furnace. A thin film heater may have a thickness of less than 5 millimeters, such as less than 2 millimeters, less than 1 millimeter, less than 0.5 millimeters, or less than 0.25 millimeters.

Independent of the specific configuration of thermal treatment device 46, the thermal treatment device may be positioned inside of housing 58 to transfer thermal energy to/from basin 14 and any contents thereof. For example, thermal treatment device 46 may be positioned inside of housing 58 and in contact with base 20 and/or sidewall(s) 22 of basin 14 such that thermal energy transfers via conduction through the base and/or sidewalls during operation of the thermal transfer device. Basin 14 can be fabricated from a thermally conductive metal, such as aluminum or stainless steel to facilitate efficient conduction of thermal energy from thermal treatment device 46 to surgical fluid inside of basin 14 through the walls of the basin.

When thermal treatment device 46 is implemented as a film heater, the film may be wrapped around at least a portion of base 20 and/or sidewall(s) 22 to position the film for transferring thermal energy into any contents within basin 14. For example, film heater may be substantially centered about base 20 of basin 14 and may cover a majority (e.g., greater than 50 percent of the base area) or substantial entirety of the base. The film heater may wrap at least partially, and in some examples fully, up the sidewall(s) 22 of basin 14. The amount of surface area of base 20 and/or sidewall(s) 22 covered by the film heater may vary, e.g., depending on the size of basin 14 and heating capacity of the film heater. In some examples, at least 25 percent of the cumulative outside surface area of basin 14 (base 20 and sidewall(s) 22) are covered with the film heater, such as at least 50 percent of the surface area.

To monitor the temperature of basin 14 and/or the contents in the basin, system 10 in the example of FIG. 6 includes temperature sensor 48. Temperature sensor 48 can sense the temperature of basin 14 and/or the temperature of the contents therein. In various examples, temperature sensor 48 may be a thermocouple, a bi-metal mechanical temperature sensor, an electrical resistance temperature sensor, an optical temperature sensor, or any other suitable type of temperature sensor. Temperature sensor 48 can generate a signal that is representative of the magnitude of the sensed temperature and communicate the generated signal to controller 42. Controller 42 may receive a signal from temperature sensor 48 indicative of the temperature measured by the sensor at periodic intervals or continuously. Accordingly, the discussion of controller 42 receiving measurement information from temperature sensor 48 at a particular time is not intended to indicate that the controller cannot or does not receive measurement information at other times.

In some examples, temperature sensor 48 is positioned on an exterior surface of basin 14 (e.g., on an opposite side of base 20 or sidewall(s) 22 from the surgical fluid) and configured to measure the temperature of the fluid through the wall surface. In other examples, however, basin 14 may include a port through which temperature sensor 48 extends to measure the temperature of the fluid directly in the basin rather than indirectly through a wall surface of the basin. This can enable more accurate temperature measurements of the contents of basin 14, e.g., for more accurately controlling thermal treatment device 46, than if temperature measurements are made indirectly through the wall surface of the basin.

Figure 10:
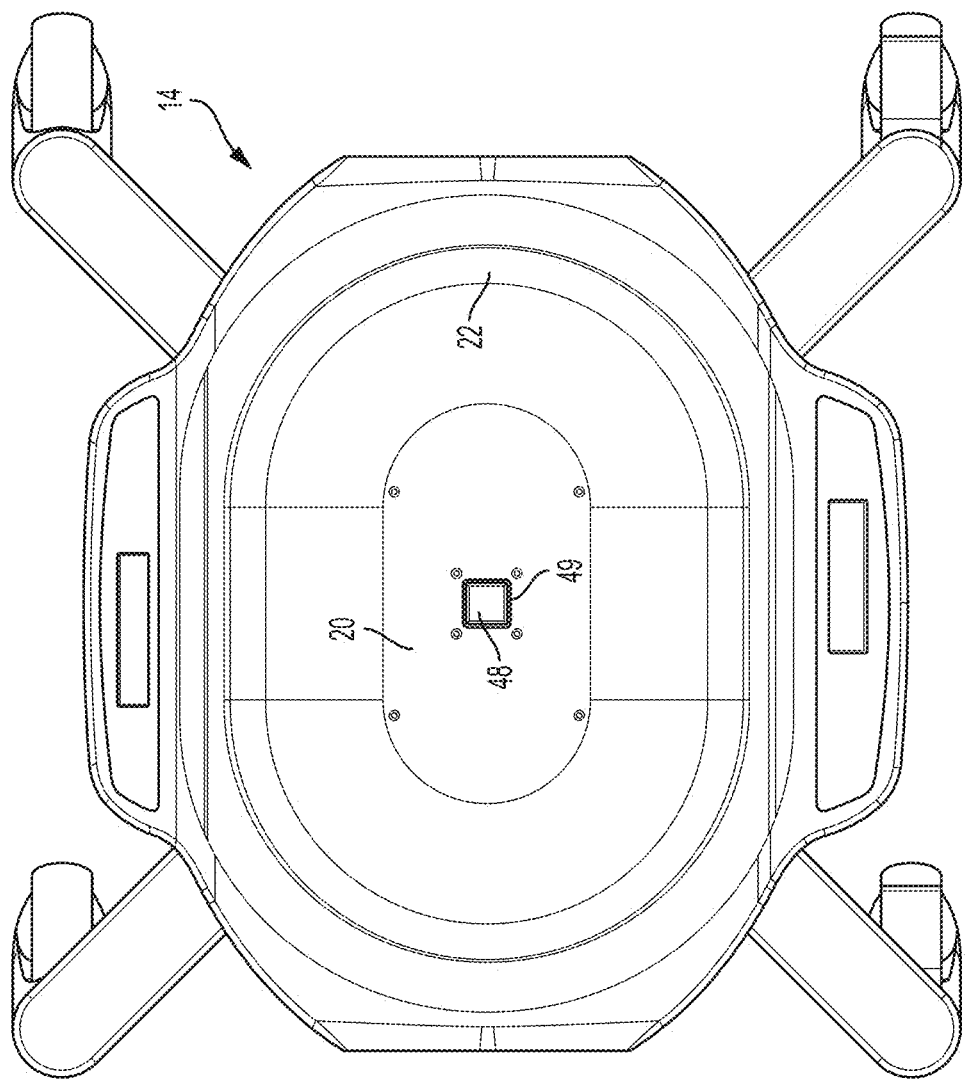
FIG. 10 is a top view of the example system in FIG. 1 illustrating an example temperature sensor arrangement.

FIG. 10 is a top view of basin 14 illustrating an example arrangement of temperature sensor 48. In the illustrated example, basin 14 defines an opening 49 extending through a wall surface of the basin (e.g., substantially centered in base 20 in the illustrated configuration). Temperature sensor 48 extends through opening 49 and may be sealed within the opening, e.g., with a rubber gasket or other polymeric material between the temperature sensor and surrounding wall surface. Temperature sensor 48 may be thermally isolated from the remainder of basin 14 by positioning a thermally insulating material between the temperature sensor and the reminder of the basin. This configuration may be useful, e.g., when a film heater is wrapped around a wall surface of basin 14, because the wall temperature may be different than the temperature of the fluid in the basin. As heat is delivered to the wall of the basin and/or fluid in the basin is equilibrating with the basin, the basin may be at a different temperature than the fluid in the basin. Accordingly, extending temperature sensor 48 through opening 49 in basin 14 and thermally isolating it from a remainder of the basin can provide a more accurate measurement of the actual temperature of fluid in the basin than if the temperature measurement is taken through the basin wall.

During operation of system 10, a clinician may engage user interface 16 to set a target temperature to which basin 14 and the contents therein are intended to be thermally adjusted to using thermal treatment device 46. For example, user interface 16 can include a temperature control that the clinician can interact with to set a target temperature. The temperature control may be a knob, switch, interactable portion of a touch screen, or other user interaction feature through which the clinician can issue commands to set a target temperature. In response to receiving the target or set temperature from the operator via user interface 16, controller 42 can perform different actions. Controller 42 may control a display associated with user interface 16 and/or display 18 to display the target temperature received from the operator. Additionally or alternatively, controller 42 can control thermal treatment device 46 to adjust the temperature of basin 14 and the contents therein until a temperature signal from temperature sensor 48 indicates that the measured temperature equals the target temperature.

In some examples, thermal treatment device 46 may heat surgical fluid in basin 14 to a temperature near a patient's normal body temperature, such as a temperature within the range of 90 degrees Fahrenheit (32.2 Celsius) to 120 degrees Fahrenheit (48.9 Celsius), such as from 95 degrees Fahrenheit (35 Celsius) to 105 degrees Fahrenheit (40.6 Celsius). The fluid initially introduced into the basin may be at ambient temperature (e.g., 60 degrees Fahrenheit (15.6 Celsius) to 75 degrees Fahrenheit (23.9 Celsius)), at an elevated temperature that basin 14 is intended to maintain, or even below ambient temperature. Controller 42 may control a display on user interface 16 if the user attempts to set the target temperature to a temperature above a threshold level, such as above 100 degrees Fahrenheit (37.8 Celsius), or above 110 degrees Fahrenheit (43.3 Celsius). In some such applications, controller 42 may prohibit the user from setting a higher temperature and may control thermal treatment device 46 to prevent heating above the threshold. In other configurations, controller 42 may allow the user to acknowledge or accept a high temperature warning provided through user interface 16 and increase the target temperature past above the threshold, e.g., up to a maximum temperature. The maximum temperature may be the maximum temperature that thermal treatment device 46 can heat fluid in basin 14 to or may be a lower temperature stored by controller 42 for safety reasons. For example, the maximum temperature may be set as a temperature less than or equal to 130 degrees Fahrenheit (54.4 degrees Celsius), such as a temperature less than or equal to 120 degrees Fahrenheit (48.9 degrees Celsius).

In some examples, controller 42 prevents or terminates operation of thermal treatment device 46 if the controller determines that no material is present in basin 14. If surgical fluid is not added to basin 14 prior to activating thermal treatment device 46, or within an appropriate period of time after activating the thermal treatment device, controller 42 may prevent or terminate operation of the device. For example, when thermal treatment device 46 is configured to heat basin 14, controller 42 can prevent the heater from dry heating the basin when there is no surgical fluid in the basin or an insufficient amount of surgical fluid is in the basin. This can help prevent damage to basin 14 and/or thermal treatment device 46.

In some examples, controller 42 determines if a sufficient amount of material (e.g., surgical fluid) is present in basin 14 based on feedback from volume measurement device 44. Controller 42 can determine the volume of material present in basin 14 based on a signal received from volume measurement device 44. Controller 42 can compare the determined volume to information stored in memory 54, for example, information indicating a threshold amount of material that needs to be present in basin 14 to allow operation of thermal treatment device 46. Controller 42 can prevent thermal treatment device 46 from activating until it determines that the threshold amount of material is present in basin 14 and/or terminate operation of thermal treatment device 46, e.g., if the threshold amount of material has not been added to the basin within a certain period of time since activating the thermal treatment device.

In other examples, controller 42 indirectly determines if a sufficient amount of material (e.g., surgical fluid) is present in basin 14 based on feedback from temperature sensor 48. Upon receiving a target temperature from an operator via user interface 16, controller 42 may activate thermal treatment device 46 and then monitor the temperature of basin 14 based on feedback from temperature sensor 48. For example, controller 42 may monitor the temperature of basin 14 from the time thermal treatment device 46 is activated, generating a temperature profile indicative of the change in the temperature of the basin over time. Controller 42 can compare the temperature profile generated during operation of thermal treatment device 46 to a temperature profile stored in memory 54. The temperature profile stored in memory 54 may be representative of the expected change in the temperature of the basin over time when an appropriate (e.g., threshold) amount of material is present in the basin. If controller 42 determines that the temperature profile generated during operation of thermal treatment device 46 deviates from the temperature profile stored in memory 54 by more than a threshold amount (e.g., 1 percent or more, 5 percent or more, 10 percent or more), controller 42 can terminate operation of thermal treatment device 46.

In some examples, such as examples when volume measurement device 44 is implemented as a weighing device, controller 42 monitors both the weight of basin 14 and any contents therein (e.g., via the weighing device) as well as the temperature profile generated during operation of thermal treatment device 46 (e.g., as measured by temperature sensor 48) to determine the contents in the basin. For example, upon receiving an indication via user interface 16 to initiate thermal adjustment, controller 42 may detect the weight of basin 14 and contents therein and further receive data indicative of the temperature of basin 14 from the time thermal treatment device 46 is activated, thereby providing a temperature profile indicative of the change in the temperature of the basin over time. If controller 42 detects weight in basin 14 but determines that the temperature profile generated during operation deviates from a temperature profile stored in memory, the controller may determine that tools are present in basin 14 that were not checked-in. Accordingly, controller 42 may respond by controlling a display or providing other user output (e.g., audible, visual message) instructing a user to remove the tools. Controller 42 may or may not prohibit continued thermal adjustment unless the user removes the tools, e.g., as confirmed by controller 42 detecting a weight change of basin 14 and the contents thereof.

As another example, if controller 42 detects weight in basin 14 but did not receive an indication via user interface 16 that fluid was to be to the basin, the controller may further compare the temperature profile generated during operation with a temperature profile stored in memory corresponding to a heating profile of the fluid. If controller 42 determines that the generated temperature profile substantially matches the stored temperature profile, the controller may determine that the initial weight measured in basin 14 is fluid that was not checked-in through user interface 16. In such a situation, controller 42 may store the measured weight corresponding to the contents of basin 14 as fluid weight/volume in a memory associated with the controller. The controller may subsequently include this weight/volume when tracking subsequent addition or removal of fluid from the basin, e.g., helping sure that the total amount of fluid withdrawn from the basin is accuracy tracked, even if the operator fails to indicate when fluid is initially being added to basin 14.

Accordingly, in some configurations, controller 42 can detect the weight of basin 14 and the contents thereof as well the temperature profile of the basin generated during thermal adjustment. Controller 42 can compare the weight and/or temperature profile to information stored in memory to determine the contents in basin 14, such as if there is only air in the basin, tools, and/or fluid in the basin. Controller 42 can provide a user output based on the determined contents of the basin.

In addition to or in lieu of controlling thermal treatment device 46 based on a measured temperature profile, controller 42 may control the rate of heating by thermal treatment device 46 based on information received from volume measurement device 44 and temperature sensor 48. For example, when volume measurement device 44 is implemented as a weighing device, controller 42 can receive information concerning the weight of basin 14 and any contents therein (e.g., surgical fluid). Controller 42 can further receive information concerning the temperature of any components in basin 14 from temperature sensor 48. Controller 42 can control the rate of heating and hence the amount of thermal energy delivered by thermal treatment device 46 based on the receive weight and temperature information.

In operation, thermal treatment device 46 can increase the temperature of fluid in basin 14 from a starting temperature to a target temperature more rapidly when there is a comparatively smaller amount of fluid in the basin then when there is a comparatively larger amount of fluid in the basin. Since there may be a thermal equilibration lag between when fluid in basin 14 reaches a target temperature and when temperature sensor 48 measures that target temperature, thermal treatment device 46 may have a tendency to overheat fluid in the basin. That is, fluid in basin 14 may be heated to a temperature above a target or set temperature before controller 42 receives a signal from temperature sensor 48 indicating that the target temperature has been reached and can control thermal treatment device 46 to cease delivering heat to the fluid. This temperature overheating phenomena may be more pronounced in instances in which there is a comparatively small amount of fluid placed in basin 14 and the fluid heats comparatively rapidly.

Figure 11:
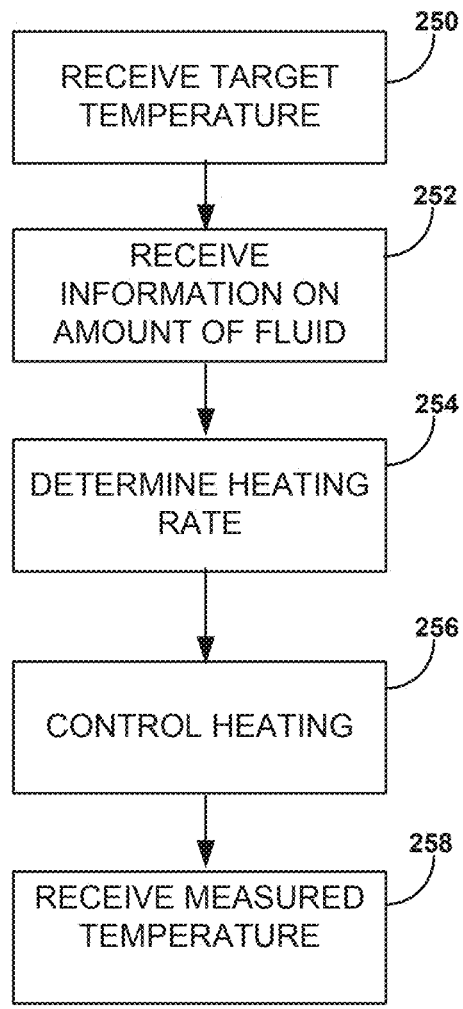
FIG. 11 is a flow diagram illustrating an example process for controlling an amount of thermal energy to be delivered to fluid being heated in the example system of FIGS. 1-3.

To help control the rate at which fluid in basin 14 is heated for more accurate heating, controller 42 may adjust the rate at which thermal treatment device 46 delivers heat based on the amount of fluid in the basin. FIG. 11 is a flow diagram illustrating an example process that system 10 may follow to control the amount of thermal energy delivered by thermal treatment device 46 to basin 14 and any contents therein.

In the example of FIG. 11, controller 42 receives target temperature information from a user via user interface 16 (250). As discussed above, the user may interact with user interface 16 using a variety of different communication media, such physical contact with the user interface, audible commands, or noncontact commands detected by the user interface. The target temperature information may specify a target temperature to which fluid in basin 14 is to be heated.

Controller 42 also receives information concerning the amount of fluid in basin 14 from volume measurement device 44 (252). For example, when volume measurement device 44 is implemented as a weighing device, controller 42 may receive information concerning the weight of basin 14 and any contents therein. If controller 42 determines that there is no fluid in basin 14 or an insufficient amount of fluid in the basin, the controller may not activate thermal treatment device 46 but may instead control a display of user interface 16 to provide instructions to the user to add fluid to the basin. In either case, controller 42 may analyze the information concerning the amount of fluid in basin 14 and use that information to control thermal treatment device 46.

With reference to information stored in memory, controller 42 may determine if the amount of fluid in basin 14 is comparatively small or if a larger amount of fluid is present in the basin and further determine a heating rate based on the amount of fluid (254). For example, controller 42 may compare weight measurement information indicative of the amount of fluid in basin 14 to one or more threshold weights stored in a memory associated with the controller. If controller 42 determines that the weight of fluid in the basin is greater than the threshold weight, the controller may control thermal treatment device 46 to heat the basin and the fluid therein at a first rate of heating. By contrast, if controller 42 determines that the weight of fluid in the basin is less than the threshold weight, the controller may control thermal treatment device 46 to heat the basin and the fluid therein at a second rate of heating less than the first rate of heating. More thermal energy is delivered to basin 14 during the first rate of heating than during the second rate of heating.

The threshold or thresholds used to set the rate of heating delivered by thermal treatment device 46 may vary, e.g., depending on the amount of thermal energy the device can supply in the size of basin 14. In some examples, the threshold weight is a weight less than 5 kg, such as a weight less than 2 kg, or a wait less than 1000 g. For example, the threshold may be 500 g or less. Additionally or alternatively, the threshold may be established based on the maximum amount of fluid that can be added to basin 14. For example, the threshold may correspond to an amount of fluid in basin 14 that is less than 50% of the maximum amount of fluid that can be added to the basin, such as less than 30% of the maximum amount. For example, the threshold may be a value corresponding to an amount of fluid in basin 14 that ranges from 2% to 30% of the maximum amount of fluid that can be added to the basin, such as from 5% to 20% of the maximum amount. The lower end of these ranges may correspond to an amount of fluid below which thermal treatment device 46 will not activate, when system 10 is so configured. In examples where the maximum volume of basin 14 is less than 10 liters, such as 5 liters, the threshold may be a value within a range from 0.25 liters to 1 liter. This may correspond to a weight value of 250 grams to 1 kilogram where the fluid is assumed to have a density of 1 Kg per liter.

In some examples, the rate of heating delivered by thermal treatment device 46 is controlled by varying the voltage or current delivered to the thermal treatment device. In other examples, the rate of heating delivered by thermal treatment device 46 is controlled by varying the duty cycle, or operating frequency, of the thermal treatment device. For example, the first rate of heating may correspond to an operating duty cycle of the thermal treatment device greater than the operating duty cycle during the second rate of heating. As examples, the operating duty cycle of thermal treatment device 46 for the first rate of heating may be a 100% duty cycle. By contrast, the operating duty cycle of thermal treatment device 46 for the second rate of heating may be less, such as a duty cycle ranging from 25% to 75%. The operating duty cycle may be considered the percentage of time during a given period during which thermal treatment device 46 is active and delivering thermal energy to basin 14 as opposed to being cycled off and not delivering thermal energy to the basin. Thermal treatment device 46 may operate at full power and cycle on and off periodically to vary the duty cycle.

With further reference to FIG. 11, controller 42 is configured to control thermal treatment device 46 to heat basin 14 and fluid therein at the rate of heating determined to be appropriate for the amount of fluid present in the basin (256). Controller 42 can receive temperature measurement information from temperature sensor 48 concerning a measured temperature of fluid in basin 14 (258). Controller 42 can continue delivering heat to the fluid in basin 14 at the rate determined to be appropriate for the amount of fluid present in the basin until the temperature of the fluid as measured via temperature sensor 48 has reached the target temperature. Upon reaching the target temperature, controller 42 can control thermal treatment device 46 to cease delivering heat to the basin and fluid therein.

Controlling the amount of heat delivered to basin 14 based on the amount of fluid determined to be present in the basin can be useful to prevent overheating of the fluid. In some examples, controller 42 is configured to control thermal treatment device 46 to modulate the rate of heating applied to the basin as the temperature measurement information from temperature sensor 48 indicates that the fluid in the basin is approaching the target temperature. Controller 42 may modulate the rate of heating by decreasing the rate of heating (e.g., progressively, step change) supplied to basin 14, independent of whatever initial rate of heating was delivered to the basin. For example, when controller 42 determines that the fluid in basin 14 is within a certain degree range from the target temperature, such as 5 degrees Fahrenheit or 10 degrees Fahrenheit from the target temperature, the controller may reduce the amount of heat delivered to the basin as compared to the amount of heat delivered prior to the fluid reaching the certain degree range. This can slow the rate of heating as the fluid approaches the target temperature and help prevent overheating.

System 10 in FIG. 6 also includes volume measurement device 44. Volume measurement device 44 is configured to measure, either directly or indirectly, the volume of material (e.g., surgical fluid) present in basin 14. Volume measurement device 44 can generate volume information concerning the amount of surgical fluid present in the basin and communicate the information to controller 42. This information can be used by controller 42 to monitor the amount of fluid added and removed from basin 14 during a procedure and, accordingly, determine the volume of surgical consumed during the procedure. Controller 42 may receive a signal from volume measurement device 44 indicative of the volume measured by the sensor at periodic intervals or continuously. The discussion of controller 42 receiving measurement information from volume measurement device 44 at a particular time is not intended to indicate that the controller cannot receive measurement information at other times.

Volume measurement device 44 can be implemented using any device that measures the amount of fluid in basin 14 from which volume can be determined. In different applications, volume measurement device 44 may be implemented using a load cell that indirectly measures volume by measuring the mass of basin 14 and contents therein, a float that rises and falls based on the level of surgical fluid in the basin, an optical or electrical resistance sensor that detects a volume level in the basin, or yet other type of sensor. For example, basin 14 may be configured with a dispensing outlet from which fluid is discharged from the basin. The fluid may be discharged directly into a patient via a tubing line or into a fluid container (e.g., graduate) that is then used to convey the fluid to the patient. A flow meter can be provided that measures the volume of fluid passing through the dispensing outlet. As another example, basin 14 may be configured with a flow meter that measures fluid volume as it is added to the basin. The amount of fluid added to the basin can be mathematically reduced by the amount of fluid remaining in the basin to determine the amount of fluid used. Independent of the configuration, volume measurement device 44 may generate an electrical signal, the magnitude of which is proportional to the volume of material present in basin 14 and/or discharging from the basin. This signal can contain volume information in that the volume of material present in basin 14 may be determined by controller 42 based on the signal.

In applications where volume measurement device 44 is implemented as a weighing device, controller 42 may subtract the weight of any drape placed in basin 14 to determine the contents of the basin. For example, controller 42 may reduce measured weights by a tare weight of basin 14 and/or drape placed therein, which can be measured at startup or stored in a memory associated with controller 42. As another example, the weight of the drape placed on basin 14 may be stored on a non-contact tag associated with the drape. Non-contact reader 50 may read the drape weight from the tag, when the drape is placed on the basin, and controller 42 can subsequently use the drape weight to decrement the measured weight.

Volume measurement device 44 can be positioned about basin 14 at a location suitable to detect the volume of surgical fluid present in basin 14. The specific location in which volume measurement device 44 is positioned can vary depending on the type of device used to measure the volume of fluid present in the basin. For example, in the case of a float that rises and falls based on the volume of fluid present in basin 14, the float can be positioned in basin 14 and connected to a transducer in housing 58 the detects and transmits the relative position of the float. As another example, in the case of a load cell that measures the weight of basin 14 and the contents thereof, the load cell may be positioned under basin 14 (e.g., in contact with base 20) to measure the weight of the basin and its contents.

When volume measurement device 44 is implemented as a weighing device, the weighing device may include any type of weighing scale capable of determining the weight or mass of an object. For example, the weighing device may be implemented using one or more load cells, strain gauges, a spring scale, an analytical scale, a hydraulic scale, a pneumatic scale, or any other device or apparatus capable of measuring the weight or mass of an object. In some examples, the weighing device comprises one or more load beams positioned under basin 14 to measure a weight of the basin and its contents. For example, a multi-load beam weighing device having two or more load cells could function as a bridge load cell. Such a weighing device could obtain the weight of basin 14 and the contents therein and provide analog strain signals to a circuit board that conditions and converts these measurements into a single mass value.

While volume measurement device 44 can be positioned at a variety of locations relative to basin 14, FIG. 12 illustrates an example arrangement of components when volume measurement device 44 is implemented as a weight measurement device. In particular, FIG. 12 is an exploded cross-sectional view of basin 14 taken along the A-A cross-sectional line indicated on FIG. 1 showing an example arrangement of components. In the illustrated example, system 10 includes basin 14, weight measurement device 44, and thermal treatment device 46. Weight measurement device 44 is illustrated as being implemented with at least one load cell which, in the cross-sectional view, is shown as to load cells 45A, 45B. Thermal treatment device 46 is illustrated as a thin-film heater wrapped at least partially about base 20 and sidewalls 22 of basin 14. Housing 58 is shown as including at least one sidewall 58A wrapping upwardly from a base 58B about the at least one sidewall 22 of the basin.

In addition, system 10 includes a mounting plate 60 that defines a first side 62 and a second side 64 opposite the first side. Mounting plate 60 is attached to basin 14 with an air gap 66 formed between the mounting plate in the basin. For example, the air gap 66 may be defined between a bottom surface of base 20 of basin 14 in the first side 62 of mounting plate 60. Weight measurement device 44 is positioned on the second side 64 of mounting plate 60. Accordingly, in this configuration, mounting plate is interposed between basin 14 and weight measurement device 44 with air gap 66 between the basin and the weight measurement device.

Configuring system 10 with an air gap 66 between basin 14 and weight measurement device 44 may be useful to help thermally isolate the weight measurement device from thermal treatment device 46 and/or the heated contents of basin 14. In different examples, air gap 66 may be entirely devoid of material or may be filled with a thermally insulative material. In either case, separating basin 14 from weight measurement device 44 may help reduce or eliminate errant weight measurements caused by the weight measurement device being at a different operating temperature for which it is calibrated. This can help improve the accuracy of weight measurements made using the device and control settings determined based on weight measurements, e.g., such as heating rates.

In some examples, air gap 66 is sized to limit the extent to which weight measurement device 44 increases in temperature above ambient temperature, e.g., when thermal treatment device 46 is operating and/or basin 14 contains heated contents. For example, air gap 66 may have a size effective to prevent weight measurement device 44 from reaching a temperature more than 5 degrees Celsius above ambient temperature when any contents in basin are heated to the temperature ranging from 90 degrees Fahrenheit (32.2 Celsius) to 120 degrees Fahrenheit (48.9 Celsius). In some examples, air gap 66 may be less than 5 cm, such as less than 2 cm. As one example, air gap 66 may range from 0.1 cm to 10 cm.

Mounting plate 60 may be attached to basin 14 in a number of different locations. In one example, mounting plate 60 may extend up and be fixedly attached under a lip formed where sidewalls 22 curve at the top of basin 14. As another example, mounting plate 60 may be fixedly attached under base 20 of basin 14, as illustrated in FIG. 12. When mounting plate 60 is attached under base 20, system 10 may include one or more spacers 68 located between the first surface 62 of the mounting plate in the bottom of base 20. The length of spacers 68 may dictate the size of air gap 66. For example, the spacers may have a top and attached to the bottom of base 20 and a bottom end attached to the top or first surface 62 of mounting plate 60.

To enable weight measurement device 44 to detect changes in the weight of the contents of basin 14, the basin may float or move relative to the weight measurement device. For example, basin 14 and mounting plate 60 attached thereto through spacers 68 (when so configured) may be configured to move upwardly and downwardly relative to weight measurement device 44 as the amount of weight in the basin varies. Second surface 64 of mounting plate 60 can press against load cells 45A, 45B with a varying degree of force depending on the amount of weight in the basin.

To prevent a user from inadvertently pulling basin 14 out of housing or shell 58, the range of travel over which the basin (and mounting plate 60 when attached) can travel may be restricted. Housing 58 may have an internal protrusion, detent, or narrowing that basin 14 and/or mounting plate 60 contacts when it reaches an upper extent of travel. As another example, one or more securing rods 70 may be attached to housing 58 and extend through mounting plate 60. Securing rods 70 may have a protrusion or widening at their top end above first surface 62 of mounting plate 60. Accordingly, basin 14 and mounting plate 60 may translate along securing rods 70 vertically upwardly until the top of the mounting plate contacts the widening of the securing rod. Basin 14 and mounting plate 60 may further translate along securing rods 70 vertically downwardly until the bottom of the mounting plate contacts a top surface of load cells 45A, 45B. In this way, basin 14 can be free-floating within the housing 58 over a restricted range of travel.

To allow basin 14 to move upwardly and downwardly over a range of travel, a top surface of the basin may be movably connected to housing 58 such that the top surface can move without coming out of the housing. In the illustrated configuration, sidewall 22 of basin 14 terminates in a lip 72 that extends generally horizontally and transitions from a generally vertically oriented remaining portion of the sidewall. Housing 58 includes a flange portion 74 extending over the terminal end of lip 72. The housing flange 74 may be configured to flex upwardly and downwardly to maintain conformance to lip 72 as basin 14 moves upwardly and downwardly. In other configurations, lip 72 may be fixedly coupled to housing 58 or basin 14 may not even include a lip.

When weight measurement device 44 is implemented using one or more load cells 45A, 45B, the load cells may be positioned at spaced apart locations from each other under base 20 and/or mounting plate 60. As one example, system 10 may include four load cells arranged in a rectangular pattern under basin 14 to measure weight substantially uniformly across the basin. The number and positioning of load cells may vary, e.g., based on the size and shape of basin 14. In different examples, weight measurement device 44 has an accuracy that measures the weight of the contents of basin 14 within 250 g of their actual weight, such as within 100 g of their actual weight, within 50 g of their actual weight, within 10 g of their actual weight, within 5 g of their actual weight, within 1 g of their actual weight, within 0.5 g of their actual weight, or within 0.1 g of their actual weight.

In operation, the volume in basin 14 as well as the weight of the contents of the basin can rise and fall as fluid is added and removed from the basin as well as when medical hardware is added and removed from the basin. To allow controller 42 to distinguish when fluid is added or removed from basin 14 as compared to when non-fluid components are added or removed, the controller may be informed of the type of material being added or removed from the basin. For example, controller 42 may be informed of the type of material being added and/or removed from basin 14 via clinician interaction with one or more user interfaces of system 10.

In some examples, user interface 16 receives a user input by a clinician to selectively indicate to controller 42 when a non-fluid component, such as a medical tool or hardware, is being added or removed from basin. The user input may be a physically movable button (e.g., switch, slide, knob), a selectable computer icon, a portion of a touch screen, or type of user input as discussed herein. In operation, the clinician may interact with the user input (e.g., depress a button), thereby providing a first indication to controller 42 that a non-fluid component is to be added or removed from basin 14. After subsequently adding the non-fluid component to basin 14 or removing the non-fluid component from the basin, the clinician may again interact with the user input (e.g., depress the button), thereby providing a second indication to controller 42 that the clinician has completed adding the non-fluid component to basin 14 or removing the non-fluid component from the basin. Alternatively, controller 42 may automatically determine without input from the user (e.g., without the user interacting with user interface 16) that the clinician has completed adding the non-fluid component to basin 14 or removing the non-fluid component from the basin after a threshold amount of time has passed since receiving the first indication, such as at least 10 seconds, at least 30 seconds, or at least one minute. In this alternative configuration, the clinician may, but need not, interact with the user input a second time after adding the non-fluid component to basin 14 or removing the non-fluid component from the basin.

Controller 42 can receive volume information from volume measurement device 44 concerning the volume of surgical fluid present in basin. In some examples, the system has a user engagement feature (e.g., button) that a user can interact with to toggle between reporting output in volume units and weight units. In the case where volume measurement device 44 is a weighing device, the volume information may be in the form of weight information. In either case, controller 42 can determine the volume of surgical fluid present in basin 14 based on the volume information received from volume measurement device 44. Controller 42 may store the determined volume in memory 54. In response to receiving the first indication via the user interface that the clinician intends to add a non-fluid component to basin 14 or remove a non-fluid component from the basin, controller 42 may receive volume information from volume measurement device 44 indicating a change in the volume of surgical fluid present in basin 14. The volume change may be caused by the clinician adding the non-fluid component to basin 14 or removing the non-fluid component from the basin, not actual changes in the amount of fluid present in the basin. Accordingly, controller 42 may disregard changes in the volume of surgical fluid determined to be present in basin 14 between receiving the first indication and receiving the second indication, which indicates that the clinician has completed adding or removing the non-fluid component to/from the basin. Controller 42 may disregard the changes in volume by referencing the volume of surgical fluid stored in memory 54 and determined to be present in basin 14 prior to receiving the first indication and setting that stored volume as the actual volume present in the basin after the non-fluid component has been added to basin 14 or removed from basin 14.

While system 10 and controller 42 can be configured to receive user input indicating when a non-fluid component is added to or removed from basin 14, the system may still accurately track the volume of fluid removed from the basin without implementing this functionality. In these applications, the user may be instructed to start (e.g., before the addition of fluid) with any non-fluid components that will be used during the procedure either in basin 14 or out of the basin. If the non-fluid components are initially added to the basin, controller 42 may determine the weight of the non-fluid components (when configured with a weight measurement device) and tare the weight or otherwise decrement the weight of the non-fluid components when subsequently determining the volume of fluid removed from the basin. The user may be instructed that non-fluid components initially present in the basin need to be returned to the basin to get an accurate measurement of the volume of fluid removed from the basin (otherwise the system may attribute the missing weight of a non-fluid component as being removed fluid). Alternatively, the user may initially start without any non-fluid components in the basin. The user may then be instructed that non-fluid components need to be removed from the basin to get an accurate measurement of the volume of fluid removed from the basin (otherwise the system may attribute a non-fluid component as being additional fluid that has actually been removed from the system). Instructing users that volume readings need to be taken with non-fluid components either "in" or "out" of basin 14 to get an accurate reading may simplify the operation and user interaction with system 10.

In addition to or in lieu of having a user input to indicate when medical hardware is being added to or removed from basin 14, system 10 may include be configured to receive a user input from a user to indicate to controller 42 when fresh surgical fluid is to be added to basin 14. The user input may be a physically movable button (e.g., switch, slide, knob), a selectable computer icon, a portion of a touch screen, or other user interface interaction as discussed herein. Additionally or alternatively, the user input may be foot actuatable peddle 40. For example, system 10 may be configured with multiple user interfaces, any of which can be used to indicate to controller 42 when fresh surgical fluid is to be added to basin 14. System 10 may include one user input that is part of user interface 16 that a clinician (e.g., sterile field personnel) can interact with to indicate to controller 42 when surgical fluid is to be added to basin 14. System 10 may also include another user input in the form of foot actuatable peddle 40 that a clinician (e.g., either sterile field personnel or non-sterile field personnel) can interact with to indicate to controller 42 when surgical fluid is to be added to basin 14.

In operation, the clinician may interact with either user input that provides an indication when fresh surgical fluid is to be added to basin 14 (e.g., by manipulating a user input on user interface 16 or actuating foot peddle 40). When the clinician initially interacts with one of the user inputs/interfaces, controller 42 may receive a first indication that fresh surgical fluid is to be added to basin 14. After subsequently adding the surgical fluid to basin 14, the clinician may again interact with either user input/interface (e.g., by manipulating a user input on user interface 16 or actuating a foot peddle 40) thereby providing a second indication to controller 42 that the clinician has completed adding the surgical fluid to basin 14. Alternatively, controller 42 may automatically determine (e.g., without the user interacting with a user input or interface) that the clinician has completed adding the fresh surgical fluid to basin 14 after a threshold amount of time has passed since receiving the first indication, such as at least 10 seconds, at least 30 seconds, or at least one minute.

In some examples, system 10 is configured to receive a signal from volume measurement device 44 upon being powered on, e.g., to determine if a user may have placed surgical fluid in basin 14 before powering the unit on. If controller 42 receives data indicating that a volume of material is present in basin 14 upon being powered on, the controller may take various responsive actions. Controller 42 may control a display of user interface 16 to issue a prompt asking the user if the detected volume is fluid that has been added to the basin. Additionally or alternatively, controller may automatically determine (e.g., without the user interacting with a user input/interface) that the detected volume is fresh fluid in the basin. For example controller 42 may control the displays to ask the user if the detected volume is surgical fluid that has been added to the basin and, if the user does not respond after a threshold amount of time, controller may automatically designate the measured volume as being fresh fluid and store the measured volume in memory. The threshold amount of time may be those amounts of time discussed above, such as at least 10 seconds, at least 30 seconds, or at least one minute. In instances where volume measurement device 44 is implemented as a weight measurement device, controller 42 may detect a volume of fluid potentially being present in basin 14 at start up by detecting a weight in basin 14 above an expected tare weight (e.g., a weight of the basin and/or drape 35 expected to be draped over the basin).

Controller 42 can receive volume information from volume measurement device 44 concerning the volume of surgical fluid present in basin before, during, and after addition of fresh surgical fluid to basin 14. Controller 42 can determine the volume of surgical fluid present in basin 14 based on the volume information received from volume measurement device 44. Controller 42 may store the determined volume in memory 54. In response to receiving the first indication that the clinician intends to add fresh surgical fluid to basin 14, controller 42 may receive volume information from volume measurement device 44 indicating an increase in the volume of surgical fluid present in basin 14. The volume change may be caused by the clinician adding fresh surgical fluid to basin 14. After receiving the second indication that the clinician has completed adding surgical fluid to basin 14, controller 42 may receive updated volume information from volume measurement device 44 indicating the volume of surgical fluid present in basin 14. The updated volume information includes the increase in volume attributable to the clinician adding fresh surgical fluid to the basin. In this way, controller 42 can distinguish between when an increase in the volume of fluid in basin 14 is attributable to the clinician adding fresh fluid to the basin and when an increase is associated with the clinician returning unused surgical fluid previously taken out of the basin.

During operation, controller 42 may detect a significant increase in volume that would be greater than normally expected by returning a non-fluid component to basin 14 and/or returning fluid taken out of the basin back to the basin. For example, fresh surgical fluid is often supplied in containers that are 500 g or 1000 g. If a user were to add a fresh container of fluid to basin 14 while neglecting to first provide a user input to the system indicating that fresh fluid was going to be added, controller 42 may be programmed to automatically (e.g., without the user interacting with a user input/interface) designate such large weight and/or volume increases as being fresh fluid added to the basin. For example, controller 42 may automatically designate large increases in volume and/or weight greater than a threshold as being fresh fluid added rather than a non-fluid component or extracted fluid being returned to the basin. The threshold may be a volume greater than 400 mL (or 400 g), such as a volume greater than 450 mL (or 450 g), or a volume greater than or equal to 500 mL (or 500 g). Other thresholds may be used. When so configured, controller 42 may control a displays to ask the user if the detected large volume is surgical fluid that has been added to the basin and, if the user does not respond after a threshold amount of time, controller may automatically designate the large volume change as being fresh fluid and store the volume increase in memory.

During a medical procedure, controller 42 can periodically or continuously receive volume information from volume measurement device 44 indicating the current volume of surgical fluid present in basin 14. For example, controller 42 may receive initial volume measurement information from volume measurement device 44 at the start of a medical procedure, e.g., indicating the amount of surgical fluid initially placed in basin 14. At one or more measurement times (e.g., continuously) during the medical procedure, controller 42 can receive updated volume information from volume measurement device 44 indicating the current volume of surgical fluid present in basin 14 at the time of measurement. Controller 42 can compare the volume of surgical fluid present in basin 14 at the measurement time to the total volume of fresh surgical fluid added to the basin (the initial volume of surgical fluid placed in basin 14 and any fresh surgical fluid subsequently added to the basin). The total volume of fresh surgical fluid added to basin 14 can be monitored by controller 42 and stored in memory 54. By determining a difference between the current volume of surgical fluid at the measurement time and the total volume of fresh surgical fluid added to the basin as of the measurement time, controller 42 can determine the volume of surgical fluid used during the medical procedure as of the measurement time.

In some examples, controller 42 controls a display associated with user interface 16 and/or display 18 to display the amount of surgical fluid used during a procedure. In different examples, controller 42 may control the display to display the weight and/or volume of surgical fluid used during the medical procedure as of the measurement time. Controller 42 may continuously update the display, e.g., as fluid is removed from basin 14 by a clinician, to provide real time information to the clinician indicating the amount of surgical fluid used during the procedure.

As mentioned above, controller 42 in the example of FIG. 6 is communicatively coupled to non-contact reader 50. Non-contact reader 50 is configured to read information stored on a non-contact tag present on a drape placed over basin 14. While the non-contact tag can be placed in physical contact with non-contact reader 50, the reader may be capable of reading information from the tag by placing the tag in close proximity to the reader without physically contacting the reader. In one example, non-contact reader 50 is implemented as a near field communication (NFC) reader. In another example, non-contact reader 50 is a frequency identification (RFID) reader or an optical reader.

Independent of the specific configuration of non-contact reader 50, the reader can read identifying information stored on a machine-readable tag present on a drape placed over basin 14. The identifying information may be in the form of a numeric code, manufacturers name or brand, or other information identifying the origin and/or type of drape to which the machine-readable tag is attached. Controller 42 can control non-contract reader 50 to read the identifying information from the machine-readable tag present on a drape placed over basin 14. Controller 42 can compare the identifying information to authenticating information stored in memory 54. The authenticating information may provide corresponding numeric codes or other information suitable for determining if the drape paced on basin 14 is authorized for use with the basin. If controller 42 determines that the identifying information read from the machine-readable tag on the drape matches the authenticating information stored on memory, the controller can allow system 10 to proceed. For example, controller 42 may allow thermal treatment device 46 to adjust the temperature of basin 14 and/or volume measurement device 44 to measure the volume of surgical fluid present in the basin.

By contrast, if controller 42 determines that the identifying information read from the machine-readable tag on the drape does not match the authenticating information stored on memory, the controller may prohibit operation of system 10. For example, controller 42 may prohibit thermal treatment device 46 from adjusting the temperature of basin 14 and/or volume measurement device 44 from measuring the volume of surgical fluid present in the basin. In some additional examples, if non-contact reader 50 does not identify a machine-readable tag, for example indicating that a drape has not been placed on basin 14 or a drape without a machine-readable tag has been placed on the basin, controller 42 may similarly prohibit operation of system 10.

In some examples, controller 42 may start a timer and/or a start time may be written to tag 38 (e.g., using a non-contact reader 50 with write functionality) upon detecting that the drape placed over basin 14 has an authorized tag. After a threshold amount of time has passed based on the timer and/or start time written on the tag, controller 42 may determine that the tag and corresponding drape has expired. The threshold amount of time may range from 1 hour to 24 hours, such as from 4 hours to 18 hours, or from 6 hours to 14 hours. Controller 42 may control user interface 16 to provide a time warning before the tag and drape are going to expire (e.g., one hour, half hour, fifteen minutes before expiration). When the tag and corresponding drape are determined to have expired, controller 42 may control thermal treatment device 46 to cease heating basin 14. Such a configuration may help ensure that the drape covering basin 14 is periodically replaced with a fresh drape to promote sterility and help ensure the integrity of the drape.

Figure 7:
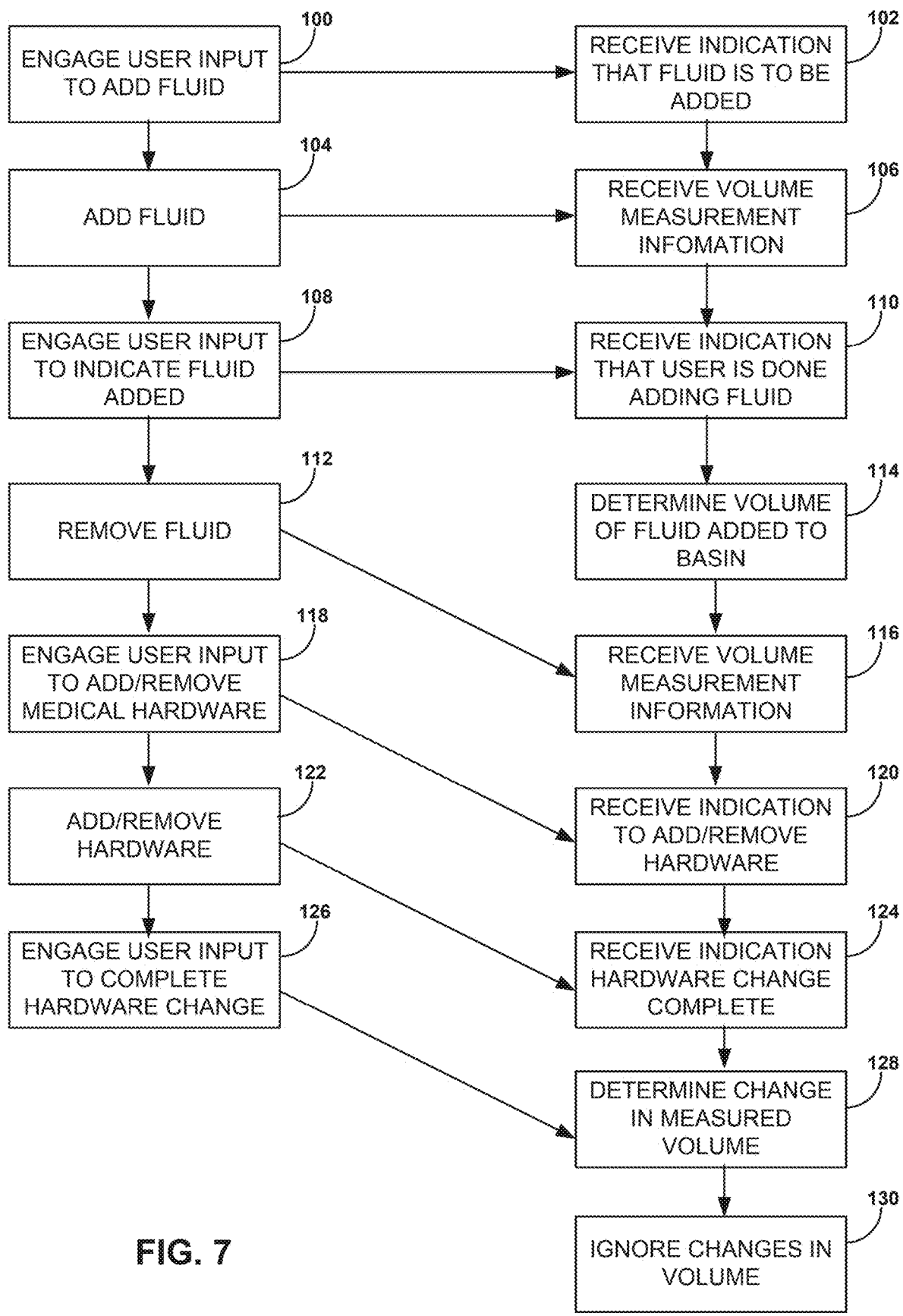
FIG. 7 is a flow diagram of an example technique that can be used to monitor the amount of surgical fluid removed from a thermal treatment device during a medical procedure.

FIG. 7 is a flow diagram of an example technique that may be used to monitor the amount of surgical fluid removed from a thermal treatment device during a medical procedure. The example technique of FIG. 7 is described with respect to thermal treatment system 10 described with respect to FIGS. 1-3 and 6, although the technique can be performed by systems having other configurations as described herein. In the example of FIG. 7, a clinician engages a user input on system 10 to indicate that the user intends to add fluid to basin 14 (100). The clinician may engage the user input by interacting with user interface 16 or by actuating foot actuatable peddle 40. In response to engaging the user input, controller 42 receives a first indication indicating that the user intends to add the surgical fluid to the basin (102). Controller 42 may control a display on system 10 providing instructions or prompts telling the user to add the surgical fluid to basin 14.

In the technique of FIG. 7, the clinician adds the surgical fluid to basin 14 (104). Controller 42 receives volume information from volume measurement device 44 as the clinician adds the surgical fluid to the basin indicating the increase in volume (106). When volume measurement device 44 is a weighing device, controller 42 may receive weight information concerning the weight of basin 14 and any contents therein. When the clinician has completed adding the surgical fluid to basin 14, the clinician again engages the user input on system 10 to indicate that the user has finished added surgical fluid to basin 14 (108). The clinician may again engage the user input by interacting with user interface 16 or by actuating foot actuatable peddle 40. In response to engaging the user input, controller 42 receives a second indication indicating that the user has completed adding fluid to the basin (110).

The technique of FIG. 7 further involves controller 42 determining the volume of surgical fluid added to basin 14 between when the clinician engaged the user interface to indicate that fluid would be added to the basin and when the clinician engaged the user interface to indicate that fluid was done being added to the basin (112). For example, when volume measurement device 44 is a weighing device, controller 42 may determine the difference in weight between basin 14 and any contents therein (e.g., medical tools with or without surgical fluid) before receiving the first indication and the weight of the basin and contents therein, including surgical fluid, after receiving the second indication. Controller 42 may determine the volume of fluid added to basin 14 by multiplying the weight change by a density of the surgical fluid stored in memory 54.

During operation of system 10, the clinician removes surgical fluid from basin 14 in the technique of FIG. 7 (114). Controller 42 receives volume measurement information from volume measurement device 44 indicating a change in the volume of present in basin 14 as the clinician removes fluid (116). For example, when volume measurement device 44 generates volume information at a measurement time, controller 42 can receive the volume measurement information and determine the volume of surgical fluid in the basin at the measurement time. Where volume measurement device 44 is a weighing device, controller 42 can receive weight information indicative of the weight of basin 14 and the contents thereof. Controller 42 can determine the change in the total volume of fluid in basin 14, e.g., by determining a difference in weight and multiplying the weight change by a density of the surgical fluid stored in memory 54. In some examples, controller 42 further controls a display on system 10 to indicate the volume of fluid consumed during the procedure.

In addition, in the technique of FIG. 7, the clinician engages a user input on system 10 to indicate that the user intends to add medical hardware (e.g., a medical tool) to basin 14 or remove medical hardware from the basin (118). The clinician may engage the user input by interacting with user interface 16. In response to engaging the user input, controller 42 receives a first indication indicating that the user intends to add the medical hardware to basin 14 or remove the medical hardware from the basin (120). The clinician subsequently adds the medical hardware to the basin or removes the medical hardware from the basin (122).

When the clinician has completed adding the medical hardware to basin 14 or removing the medical hardware from the basin, the clinician again engages the user input on user interface 16 to indicate that the user has finished added or removing the medical hardware (124). In response to engaging the user input, controller 42 receives a second indication indicating that the user has completed adding medical hardware to basin 14 or removing medical hardware from the basin (126). Thereafter, controller 42 can determine changes in the measured volume of surgical fluid in basin 14 between when the clinician engaged the user interface to indicate that medical hardware would be added or removed from the basin and when the clinician engaged the user interface to indicate that the hardware change was complete (128). For example, when volume measurement device 44 is a weighing device, controller 42 may determine the difference in weight between basin 14 and the contents thereof before receiving the first indication and the weight of the basin and its contents after receiving the second indication. The change in weight may be attributable to the addition or removal of medical hardware from basin 14 instead of any addition or removal of medical fluid from the basin.

In the technique of FIG. 7, controller 42 disregards changes in the measured volume between when the clinician engaged the user interface to indicate that medical hardware would be added or removed from the basin and when the clinician engaged the user interface to indicate that the hardware change was complete (130). Controller 42 may disregard the changes in volume by referencing the volume of surgical fluid determined to be present in basin 14 prior to receiving the first indication (e.g., and stored in memory 54) and setting the stored volume as the actual volume present in the basin after the medical hardware has been added or removed from basin 14. Accordingly, controller 42 can control the display of system 10 to the volume of surgical fluid consumed during the procedure and reported on the display does not change when adding medical hardware to basin 14 or removing medical hardware from the basin.

Figure 8A:
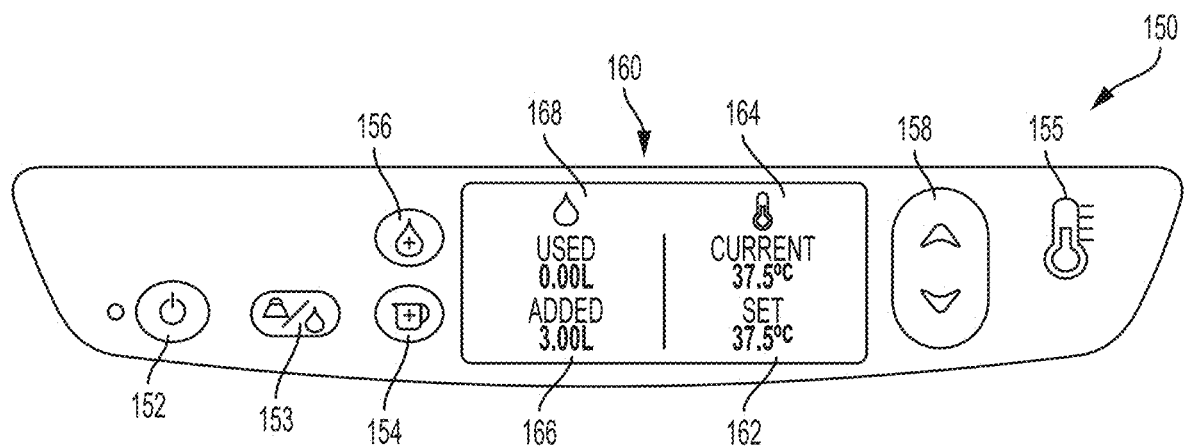
FIG. 8A is an example user interface that can be used on the example system of FIGS. 1-3.

FIG. 8A is an example user interface 150 that can be used as user interface 16 in system 10. User interface 150 includes a power button 152 to turn system 10 on and off, a first user input 154, a second user input 156, a temperature control 158, and a display 160. First user input 154 and second user input 156 are both illustrated in the form of depressible buttons, although other user input configurations can be used as described herein. Temperature control 158 allows the clinician to set the target temperature to which surgical fluid in basin 14 is heated, including incrementing and decrementing the target temperature. In addition, user interface 150 includes a temperature indication light 155 that indicates when surgical fluid in basin 14 is at the target temperature (e.g., by turning on/off or by changing color). User interface 150 also includes a service button 153 that allows a user to toggle display 160 to a service/options menu from which various programming options and preferences can be selected.

First user input 154 is manipulable (e.g., depressible) by a clinician to indicate that a non-fluid component, such as medical tools, are to be added or removed from basin 14. Pressing first user input 154 a first time informs system 10 that a medical tool is to be added or removed from basin 14. Pressing first user input 154 a second time informs system 10 that the clinician has completed adding the medical tool to basin 14 or removing the medical tool from the basin (regardless of whether the clinician actually adds or removes a tool).

Second user input 156 is manipulable (e.g., depressible) by a clinician to indicate that fresh surgical fluid is to be added to basin 14. Pressing second user input 156 a first time informs system 10 that the surgical fluid is to be added to basin 14. Pressing second user input 156 a second time informs system 10 that the clinician has completed adding the surgical fluid to basin 14 (regardless of whether the clinician actually adds the fluid). The clinician may engage foot actuatable peddle 40 instead of second user input 156 to inform the system that surgical fluid is to be added to basin 14 and/or has been added to the basin.

Display 160 can display information entered into or generated by system 10. For example, in FIG. 8A, display 160 displays the target temperature 162 entered into system 10 via temperature control 158 as well as the actual temperature 164 of surgical fluid in basin 14 measured by temperature sensor 48 (FIG. 6). Display 160 also displays the total (cumulative) volume of surgical fluid 166 added to basin 14 during the procedure and the volume of surgical fluid used (removed) 168 from the surgical basin during the procedure. Accordingly, the difference between the total volume of surgical fluid 166 added to basin 14 and the volume of surgical fluid used 168 is the volume of surgical fluid remaining in the basin. In other configurations, display 160 can display the amount of surgical fluid added to basin 14 and/or removed from the basin in different formats, such as by weight, graphical chart, or the like.

Figure 8B:
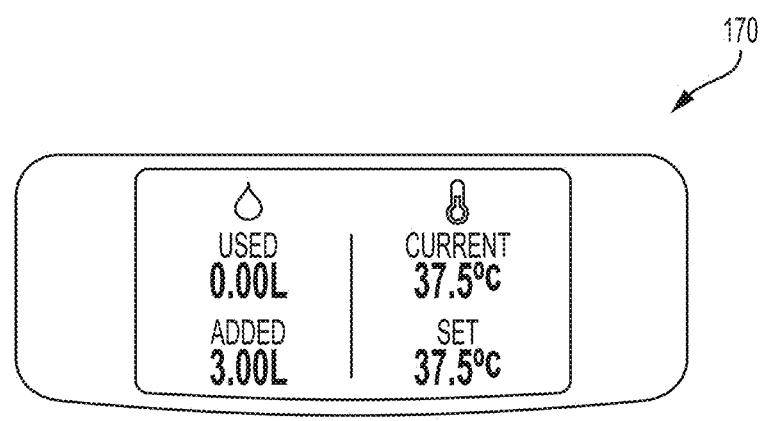
FIG. 8B is an example display that can be used on the example system of FIGS. 1-3.

FIG. 8B is an example display 170 that can be used as display 18 in system 10. As shown, display 170 can be configured to display the same information as display 160 on user interface 150. As discussed above, however, display 170 may be positioned on a different side of basin 14 than user interface 150, allowing clinicians working on different sides of the basin to see information entered into or generated by the system.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A thermal treatment system comprising:
a basin configured to receive and hold a material to be heated;
a thermal treatment device thermally coupled to the basin and configured to adjust a temperature of the material to be heated in the basin;
a weight measurement device positioned to measure a weight of the basin and any contents therein;
a temperature sensor;
a user interface; and
a controller in communication with the user interface, the temperature sensor, the thermal treatment device, and the weight measurement device, wherein the controller is configured to:
receive a target temperature via the user interface to which any contents in the basin are to be heated;
receive weight measurement information from the weight measurement device concerning the weight of the basin and any contents therein;
receive temperature measurement information from the temperature sensor concerning a measured temperature of any contents in the basin;
compare weight measurement information from the weight measurement device to a threshold weight stored in memory;
and
control the thermal treatment device to heat the basin and any contents therein to the target temperature based on weight measurement information received from the weight measurement device and temperature measurement information received from the temperature sensor by controlling the thermal treatment device to heat the basin and any contents therein at a first rate of heating when weight measurement information is greater than the threshold weight and controlling the thermal treatment device to heat the basin and any contents therein at a second rate of heating less than the first rate of heating when the weight measurement information is less than the threshold weight.

2. The system of claim 1, wherein the controller is configured to control a rate of heating by adjusting a duty cycle of the thermal treatment device.

3. The system of claim 1, wherein the controller is configured to:
control the thermal treatment device to heat at the first rate of heating by operating the thermal treatment device at a 100% duty cycle, and
control the thermal treatment device to heat at the second rate of heating by operating the thermal treatment device at a duty cycle ranging from 25% to 75%.

4. The system of claim 1, wherein the controller is configured to control the thermal treatment device to modulate a rate of heating applied to the basin as the temperature measurement information indicates the contents of the basin are approaching the target temperature.

5. The system of claim 1, wherein the threshold weight is within a range from 5 percent to 20 percent of a maximum weight as measured when the basin is full of the material to be heated.

6. The system of claim 1, wherein the threshold weight is less than 1000 grams.

7. The system of claim 1, wherein the user interface is configured to be physically, audibly, or optically engaged by a user.

8. The system of claim 1, wherein the controller is configured to prevent heating of the material in the basin above a maximum temperature.

9. The system of claim 8, wherein the maximum temperature is a temperature less than or equal to 130 degrees Fahrenheit (54.4 degrees Celsius).

10. The system of claim 9, wherein:
the controller is configured to receive the target temperature that is above a high temperature warning threshold but below the maximum temperature,
in response to receiving the target temperature, control the user interface to issue a high temperature warning, and only after receiving a user acknowledgement of the high temperature warning, control the thermal treatment device to heat the material in the basin to a temperature above the high temperature warning threshold but below the maximum temperature.

11. The system of claim 1, wherein the temperature sensor extends through a sealed opening in the base of the basin and is thermally isolated from a base of the basin.

12. The system of claim 1, wherein the thermal treatment device comprises a film heater wrapped at least partially around the basin, and the film heater is configured to heat the material in the basin from ambient temperature to a temperature ranging from 90 degrees Fahrenheit (32.2 Celsius) to 120 degrees Fahrenheit (48.9 Celsius).

13. The system of claim 1, wherein the basin has a capacity of less than ten liters.

14. The system of claim 1, wherein the weight measurement device comprises at least one load cell positioned under the basin.

15. The system of claim 14, wherein the at least one load cell comprises a plurality of load cells positioned at spaced apart locations from each other under the basin.

16. The system of claim 1, further comprising a housing surrounding the basin and enclosing the thermal treatment device and the weight measurement device.

17. The system of claim 16, wherein the housing comprises a base and at least one sidewall and the base and at least one sidewall of the housing wrap about the base and the at least one sidewall of the basin.

18. The system of claim 16, wherein the housing is supported by and vertically elevated above a base mounted on wheels.

* * * * *